(12) United States Patent
Schneider et al.

(10) Patent No.: US 10,889,544 B2
(45) Date of Patent: *Jan. 12, 2021

(54) IONIC LIQUIDS COMPRISING HETEROAROMATIC ANIONS

(71) Applicant: UNIVERSITY OF NOTRE DAME DU LAC, Notre Dame, IN (US)

(72) Inventors: William F. Schneider, Granger, IN (US); Joan F. Brennecke, Granger, IN (US); Edward J. Maginn, South Bend, IN (US); Elaine Vazquez, Chicago, IL (US); Burcu Gurkan, South Bend, IN (US); Erica Price, Mishawaka, IN (US); Brett Goodrich, Mishawaka, IN (US)

(73) Assignee: UNIVERSITY OF NOTRE DAME DU LAC, Notre Dame, IN (US)

( * ) Notice: Subject to any disclaimer, the term of this patent is extended or adjusted under 35 U.S.C. 154(b) by 22 days.

This patent is subject to a terminal disclaimer.

(21) Appl. No.: 16/121,239

(22) Filed: Sep. 4, 2018

(65) Prior Publication Data

US 2019/0031608 A1    Jan. 31, 2019

Related U.S. Application Data

(60) Continuation of application No. 15/802,360, filed on Nov. 2, 2017, now Pat. No. 10,259,788, which is a
(Continued)

(51) Int. Cl.
*B01D 53/02* (2006.01)
*C07D 207/32* (2006.01)
(Continued)

(52) U.S. Cl.
CPC ....... *C07D 207/32* (2013.01); *B01D 53/1456* (2013.01); *B01D 53/1493* (2013.01);
(Continued)

(58) Field of Classification Search
CPC .......... B01D 2252/30; B01D 2257/302; B01D 2257/404; B01D 2257/504;
(Continued)

(56) References Cited

U.S. PATENT DOCUMENTS 3,294,814 A   12/1966 Reicheneder et al.
3,426,754 A   2/1969 Bierenbaum et al.
(Continued)

FOREIGN PATENT DOCUMENTS

EP   0850933 A1   7/1998
EP   1880754 A1   1/2008
(Continued)

OTHER PUBLICATIONS

Martin. Angel et al. "Thermodynamic analysis of absorption refrigeration cycles using ionic liquid+ supercritical CO2 pairs", The Journal of Supercritical Fluids. 2010. vol. 55. No. 2. pp. 852-859.
(Continued)

*Primary Examiner* — Christopher P Jones
(74) *Attorney, Agent, or Firm* — Michael Best & Friedrich LLP

(57) ABSTRACT

Some embodiments described herein relate to ionic liquids comprising an anion of a heteroaromatic compound such as optionally substituted pyrrolide, optionally substituted pyrazolide, optionally substituted indolide, optionally substituted phospholide, or optionally substituted imidazolide. Methods and devices for gas separation or gas absorption related to these ionic liquids are also described herein.

9 Claims, 11 Drawing Sheets

Related U.S. Application Data division of application No. 13/505,730, filed as application No. PCT/US2010/055330 on Nov. 3, 2010, now Pat. No. 9,951,008.

(60) Provisional application No. 61/257,795, filed on Nov. 3, 2009.

(51) Int. Cl.

| | |
|---|---|
| *B01D 53/14* | (2006.01) |
| *C07D 207/323* | (2006.01) |
| *C07D 207/325* | (2006.01) |
| *C07D 207/33* | (2006.01) |
| *C07D 207/34* | (2006.01) |
| *C07D 207/46* | (2006.01) |
| *C07D 209/08* | (2006.01) |
| *C07D 231/12* | (2006.01) |
| *C07D 233/58* | (2006.01) |
| *C07F 9/54* | (2006.01) |

(52) U.S. Cl.
CPC ..... *C07D 207/323* (2013.01); *C07D 207/325* (2013.01); *C07D 207/33* (2013.01); *C07D 207/34* (2013.01); *C07D 207/46* (2013.01); *C07D 209/08* (2013.01); *C07D 231/12* (2013.01); *C07D 233/58* (2013.01); *C07F 9/5407* (2013.01); *B01D 2252/30* (2013.01); *B01D 2257/302* (2013.01); *B01D 2257/404* (2013.01); *B01D 2257/504* (2013.01); *B01D 2258/0283* (2013.01); *Y02C 20/40* (2020.08); *Y02E 20/32* (2013.01); *Y02P 20/151* (2015.11)

(58) Field of Classification Search
CPC ........ B01D 2258/0283; B01D 53/1456; B01D 53/1493; C07D 207/32; C07D 207/323; C07D 207/325; C07D 207/33; C07D 207/34; C07D 207/46; Y02C 10/04
See application file for complete search history.

(56) References Cited

U.S. PATENT DOCUMENTS

| | | | |
|---|---|---|---|
| 3,801,404 | A | 4/1974 | Druin et al. |
| 3,839,516 | A | 10/1974 | Williams et al. |
| 3,843,761 | A | 10/1974 | Bierenbaum et al. |
| 3,843,762 | A | 10/1974 | Sleigh |
| 3,920,785 | A | 11/1975 | Druin et al. |
| 4,055,696 | A | 10/1977 | Kamada et al. |
| 4,255,376 | A | 3/1981 | Soehngen |
| 4,257,997 | A | 3/1981 | Soehngen et al. |
| 4,359,510 | A | 11/1982 | Taskier |
| 4,405,688 | A | 9/1983 | Lowery et al. |
| 4,438,185 | A | 3/1984 | Taskier |
| 4,621,089 | A | 11/1986 | Ward et al. |
| 4,837,238 | A | 6/1989 | Markwell et al. |
| 5,228,897 | A | 7/1993 | Korte et al. |
| 6,329,342 | B1 | 12/2001 | Kauffman et al. |
| 6,391,988 | B1 | 5/2002 | Hlatky |
| 6,415,614 | B1 | 7/2002 | Greenfield et al. |
| 6,579,343 | B2 | 6/2003 | Brennecke et al. |
| 6,639,076 | B1 | 10/2003 | Hauser et al. |
| 7,053,232 | B2 | 5/2006 | Moulton |
| 2001/0031875 | A1 | 10/2001 | Kitazume |
| 2005/0129598 | A1 | 6/2005 | Chinn et al. |
| 2005/0131118 | A1 | 6/2005 | Moulton et al. |
| 2005/0196671 | A1 | 9/2005 | Paonessa et al. |
| 2006/0197053 | A1 | 9/2006 | Shiflett et al. |
| 2006/0211678 | A1 | 9/2006 | Ahmed et al. |
| 2007/0093462 | A1 | 4/2007 | Rogers et al. |
| 2007/0144186 | A1 | 6/2007 | Shiflett et al. |
| 2007/0295478 | A1 | 12/2007 | Shiflett et al. |
| 2008/0028777 | A1 | 2/2008 | Boesmann et al. |
| 2009/0005410 | A1 | 1/2009 | Charvat et al. |
| 2009/0042910 | A1 | 2/2009 | Jung et al. |
| 2009/0137580 | A1 | 5/2009 | Imamura et al. |
| 2009/0325956 | A1 | 12/2009 | Taniguchi et al. |
| 2010/0044620 | A1 | 2/2010 | Rached |
| 2010/0152159 | A1 | 6/2010 | Mitchell et al. |
| 2011/0126563 | A1 | 6/2011 | Tang et al. |
| 2012/0134905 | A1 | 5/2012 | Kalb |
| 2012/0204717 | A1 | 8/2012 | Dinnage |
| 2012/0222557 | A1 | 9/2012 | Schneider et al. |
| 2012/0264605 | A1 | 10/2012 | Rogers et al. |
| 2013/0058852 | A1 | 3/2013 | Atkins et al. |

FOREIGN PATENT DOCUMENTS

| | | |
|---|---|---|
| EP | 1950271 A1 | 7/2008 |
| WO | WO 2005113496 A1 | 12/2005 |
| WO | WO 2008044767 A1 | 4/2008 |
| WO | WO 2008124042 A1 | 10/2008 |
| WO | WO 2010023413 A1 | 3/2010 |

OTHER PUBLICATIONS

Gurkan et al., "Molecular Design of High Capacity, Low Viscosity, Chemically Tunable Ionic Liquids for CO2 Capture", The Journal of Physical Chemistry Letters. Dec. 3, 2010. 1(24):3494-3499.

International Search Report and Written Opinion issued in application No. PCT/US2014/058366 dated Jan. 16, 2015 (UND.013WO).

International Search Report and Written Opinion issued in application No. PCT/US2014/064172 dated Feb. 12, 2015 (UND.014WO).

Wang et al., "Carbon Dioxide Capture by Superbase-Derived Protic Ionic Liquids", Angewandte Chemie, International Edition, Coden: ACIEF5, 49(34):5978-5981 (Aug. 9, 2010).

Steinbach et al., "Labeling of Aromatic Compounds with Carbon-11 in Ring Position", Synthesis 1h and Applications of Isotopically Labelled Compounds, Proceedings of the International Symposium, ?, Dresden Germany Jun. 18-22, 2000.

International Search Report and Written Opinion issued in application No. PCT/US2010/055330 dated Feb. 18, 2011.

IONIC LIQUIDS COMPRISING HETERAROMATIC ANIONS

CROSS-REFERENCE TO RELATED APPLICATION(S)

This application is a continuation of U.S. patent application Ser. No. 15/802,360, filed on Nov. 2, 2017, which is a divisional of U.S. patent application Ser. No. 13/505,730, filed on May 2, 2012, now U.S. Pat. No. 9,951,008, issued on Apr. 24, 2018, which is a U.S. National Stage Entry under 35 U.S.C. § 371 of International Patent Application No. PCT/US2010/055330, filed on Nov. 3, 2010, which claims priority to U.S. Provisional Patent Application No. 61/257,795, filed on Nov. 3, 2009, the entire contents of each of which are fully incorporated herein by reference.

STATEMENT REGARDING FEDERALLY SPONSORED R&D

The U.S. Government has a paid-up license in this invention and the right in limited circumstances to require the patent owner to license others on reasonable terms as provided for by the terms of DE-FC26-07NT43091 awarded by the United States Department of Energy.

BACKGROUND OF THE INVENTION

Field of the Invention

The embodiments described herein relate to ionic liquids, such as ionic liquids used for separating or absorbing acidic gases.

Description of the Related Art

Ionic liquids are increasingly being used for a number of applications, such as for separation or purification of gases, or for other applications that involve the absorption of one or more gases. Of particular interest is the separation of acidic gases, such as oxides of carbon, nitrogen, or sulfur. These gases are common impurities in many gas mixtures, and are common air pollutants. For example, carbon capture and sequestration, the removal of carbon dioxide from combustion exhaust, or from air, to reduce the greenhouse effect on global warming, is of particular interest.

The atmospheric concentration of $CO_2$ has increased unabated since the dawn of the industrial revolution, due primarily to $CO_2$ emissions from the combustion of fossil fuels, and this growing carbon burden may have significant implications for the global climate. While the development of a carbon-neutral infrastructure may be a long-term solution to this problem, the increasing world demand for energy and the ready availability of fossil fuels—in particular coal-make it highly likely that fossil fuel combustion will continue to be a substantial fraction of the energy portfolio for the foreseeable future. In this environment, alternative approaches to managing $CO_2$ emissions become desirable.

For coal-fired power plants and other point source emitters, post-combustion carbon capture may be the most straightforward and promising route to limiting $CO_2$ release, but practical carbon capture may depend on the discovery of energy-efficient means of separating $CO_2$ from the other gaseous components of a flue gas. For example a typical 500 MW coal-fired power plant produces about 22 kmol s$^{-1}$ of flue gas containing ~15% $CO_2$ in $N_2$, $O_2$, $H_2O$ and other trace gases at near ambient temperature and pressure. Separating $CO_2$ from this stream may consume more than 30% of the power of the plant using presently available amine absorption technologies, far above the theoretical minimum work of separation.

Many ionic liquids may be unsuitable for industrial removal of carbon dioxide and other acidic gases because they may become highly viscous when the acidic gas is absorbed, or because they may not be suitable for absorption of the gas and the subsequent removal of the gas to store the gas and/or to recycle the ionic liquid. Therefore, there is a need for additional ionic liquids which may improve one or more of these properties.

SUMMARY OF THE INVENTION

Some embodiments provide an ionic liquid comprising an anion selected from: optionally substituted pyrrolide optionally, substituted pyrazolide, optionally substituted indolide, optionally substituted phospholide, or optionally substituted imidazolide.

Some embodiments provide an ionic liquid comprising an anion represented by a Formula 1 or Formula 2:

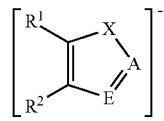
(Formula 1)

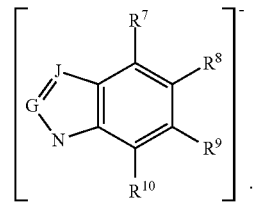
(Formula 2)

Some embodiments related to an anionic liquid comprising an anion represented by Formula A:

[Het··CO$_2$]$^-$     (Formula A);

wherein ·· represents a covalent or non-covalent bonding interaction; and Het is optionally substituted heteroaryl.

Some embodiments relate to an ionic liquid comprising an anion represented by a Formula 7 or Formula 8:

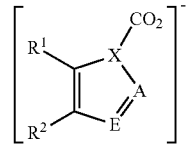
(Formula 7)

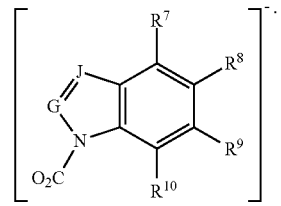
(Formula 8)

In Formulas 1, 2, 7, and 8, X is N or P; A is N or $CR^3$; E is N or $CR^4$; G is N or $CR^5$; J is N or $CR^6$; and $R^1$, $R^2$, $R^3$, $R^4$, $R^5$, $R^6$, $R^7$, $R^8$, $R^9$, and $R^{10}$ are independently halo, CN, CNO, NCO, $NO_2$, $R^{11}$, $OR^{11}$, $SR^{11}$, $NR^{12}R^{13}$, —YC(O)$ZR^{11}$, $SO_2R^{11}$, $SO_3R^{11}$, or $SO_2NR^{12}R^{13}$; Y is a single bond, optionally substituted $C_{1-6}$ hydrocarbyl, —N($R^{12}$)—, O, or S; Z is a single bond, —N($R^{12}$)—, O, or S; each $R^{11}$ is H or optionally substituted $C_{1-12}$ hydrocarbyl; and each $R^{12}$ and each $R^{13}$ is independently H or optionally substituted $C_{1-6}$ hydrocarbyl.

Some embodiments relate to a method of separating an acidic gas from a mixture of gases, comprising: providing sufficient contact between the mixture of gases and an ionic liquid described herein to allow at least a portion of the acidic gas to be absorbed by the ionic liquid to provide a purified gas; and collecting or diverting for use the purified gas and/or the acidic gas.

Some embodiments provide a method of separating an acidic gas from a combustion exhaust, comprising: providing an exhaust from combustion of a carbon-based fuel, wherein the exhaust comprises the acidic gas; and providing sufficient contact between the exhaust and an ionic liquid described herein to allow at least a portion of the acidic gas to be absorbed by the ionic liquid.

Some embodiments relate to a method of separating an acidic gas from a mixture of gases, comprising: providing sufficient contact between the mixture of gases and an ionic liquid described herein to allow at least a portion of the acidic gas to be absorbed by the ionic liquid; and recovering the acidic gas from the ionic liquid by applying at least one of heat or reduced pressure to the ionic liquid.

Some embodiments relate to a method of cooling an enclosed volume comprising compressing and expanding a gas comprising carbon dioxide in the presence of an ionic liquid described herein.

Some embodiments provide a gas separation device comprising: a flow component configured to provide a flow of a mixture of gases, wherein the mixture of gases comprises an acidic gas; a separation component, in fluid communication with the flow component, configured to allow the flow of the mixture of gases to pass through the separation component from the flow component; and the ionic liquid described herein, coupled to the separation component; wherein the device is configured to provide sufficient contact between the mixture of gases and the ionic liquid to remove at least a portion of the acidic gas from the mixture of gases.

Some embodiments provide a combustion device comprising: a combustion vessel configured to contain a combustion reaction; an exhaust component, in fluid communication with the combustion vessel, which is configured to allow exhaust from the combustion reaction to escape from the combustion vessel, wherein the exhaust comprises an acidic gas; and the ionic liquid described herein, coupled to the exhaust component; wherein the device is configured to provide sufficient contact between the exhaust and the ionic liquid to remove at least a portion of the acidic gas from the exhaust.

DETAILED DESCRIPTION OF THE PREFERRED EMBODIMENT

Figure 1:
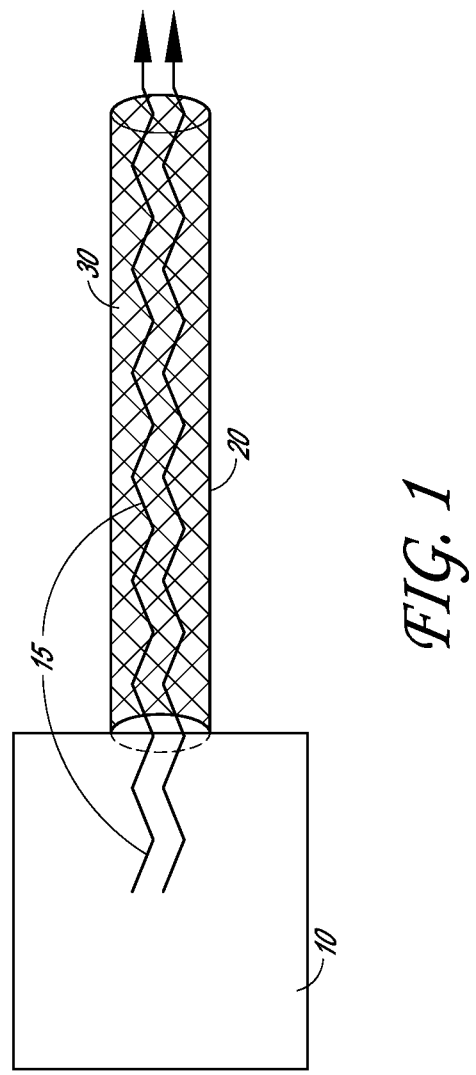
FIG. 1 is an example of an embodiment of a gas separation device described herein.

As used herein the term "ionic liquid" has the ordinary meaning understood by a person of ordinary skill in the art. In some embodiments, the term "ionic liquid" may include a nonpolymeric salt that is reasonably fluid under ambient conditions. The salt may comprise monovalent or polyvalent anions or cations. In addition, the ionic liquid may be a single salt or a mixture of salts. In some embodiments, the ionic liquid is a liquid at a temperature in the range of from about 1° C. to about 100° C. and at a pressure of about 1 atmosphere. It is appreciated that some ionic liquids may have melting points above ambient temperatures or well below 1° C. However, ionic liquids may be distinguished from conventional "molten salts", such as sodium chloride, requiring excessive temperatures (e.g. greater than about 250° C.) to achieve a liquid phase. In some embodiments, ionic liquids may have negligible vapor pressures under ambient conditions and may often form stable liquids at temperatures up to about 300° C. In some embodiments, ionic liquids may also have a wide range of miscibilities with organic solvents and water. However, an ionic liquid is not necessarily soluble in either organic solvents or water.

Unless otherwise indicated, when a chemical structural feature such as hydrocarbyl or an anion of heteroaryl moieties such as pyrazole, indole, phosphole, imidazole, is referred to as being "optionally substituted," it is meant that the feature may have no substituents (i.e. be unsubstituted) or may have one or more substituents. A feature that is "substituted" has one or more substituents. The term "substituent" has the ordinary meaning known to one of ordinary skill in the art. In some embodiments, the substituent is an ordinary organic moiety known in the art, which may have a molecular weight (e.g. the sum of the atomic masses of the atoms of the substituent) of less than: about 500 g/mol, about 300 g/mol, about 200 g/mol, about 100 g/mol, or about 50 g/mol. In some embodiments, the substituent comprises: about 0-30, about 0-20, about 0-10, or about 0-5 carbon atoms; and about 0-30, about 0-20, about 0-10, or about 0-5 heteroatoms independently selected from: N, O, S, P, Si, F, Cl, Br, I, and combinations thereof; provided that the substituent comprises at least one atom selected from: C, N, O, S, P, Si, F, Cl, Br, and I. Examples of substituents include, but are not limited to, alkyl, alkenyl, alkynyl, carbazolyl, aryl, heteroaryl, heteroalicyclyl, aralkyl, heteroaralkyl, (heteroalicyclyl)alkyl, hydroxy, protected hydroxy, alkoxy, aryloxy, acyl, ester, mercapto, alkylthio, arylthio, cyano, halogen, carbonyl, thiocarbonyl, O-carbamyl, Ncarbamyl, Othiocarbamyl, Nthiocarbamyl, Camido, Namido, S-sulfonamido, Nsulfonamido, Ccarboxy, protected C-carboxy, Ocarboxy, isocyanato, thiocyanato, isothiocyanato, nitro, silyl, sulfenyl, sulfinyl, sulfonyl, haloalkyl, haloalkoxyl, trihalomethanesulfonyl, trihalomethanesulfonamido, and amino, including mono and disubstituted amino groups, and the protected derivatives thereof. In some embodiments, two substituents may together form an aliphatic or an aromatic ring.

The term "heteroaryl" also has the meaning understood by a person of ordinary skill in the art, and in some embodiments, may refer to an aromatic ring which has one or more heteroatoms in the ring or ring system. Examples of "heteroaryl" may include, but are not limited to, pyridinyl, furyl, thienyl, oxazolyl, thiazolyl, imidazolyl, quinolinyl, benzofuranyl, benzothienyl, benzooxazolyl, benzothiazolyl, benzoimidazolyl, etc.

The parent ring structures associated with certain optionally substituted anionic ring systems are depicted below. The name of each anion is shown below the structure of the anion. If the ring structure is substituted, a substituent may be present on any ring carbon atom.

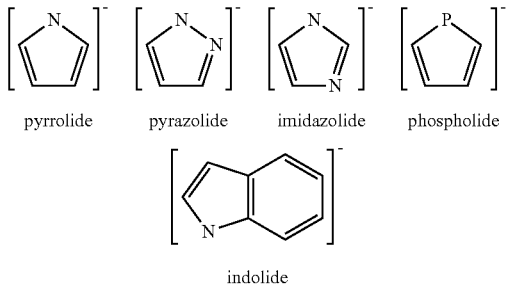

pyrrolide    pyrazolide    imidazolide    phospholide indolide

As used herein, the term "halo" refers to a halogen, such as F, Cl, Br, or I.

As used herein, the term "hydrocarbyl" refers to a moiety composed of carbon and hydrogen. Hydrocarbyl includes alkyl, alkenyl, alkynyl, aryl, etc., and combinations thereof, and may be linear, branched, cyclic, or a combination thereof. Hydrocarbyl may be bonded to any other number of moieties (e.g. be bonded to 1 other group, such as —$CH_3$, —CH=$CH_2$, etc.; 2 other groups, such as -phenyl-, —CαC—, etc.; or any number of other groups) that the structure may bear, and in some embodiments, may contain from one to thirty-five carbon atoms. Examples of hydrocarbyl groups include but are not limited to $C_1$ alkyl, $C_2$ alkyl, $C_2$ alkenyl, $C_2$ alkynyl, $C_3$ alkyl, $C_3$ alkenyl, $C_3$ alkynyl, $C_4$ alkyl, $C_4$ alkenyl, $C_4$ alkynyl, $C_5$ alkyl, $C_5$ alkenyl, $C_5$ alkynyl, $C_6$ alkyl, $C_6$ alkenyl, $C_6$ alkynyl, phenyl, etc.

As used herein, the term "alkyl" refers to a moiety composed of carbon and hydrogen containing no double or triple bonds. Alkyl may be linear, branched, cyclic, or a combination thereof, may be bonded to any other number of moieties (e.g. be bonded to 1 other group, such as —$CH_3$, 2 other groups, such as —$CH_2$—, or any number of other groups) that the structure may bear, and in some embodiments, may contain from one to thirty-five carbon atoms.

Examples of alkyl groups include but are not limited to $CH_3$ (e.g. methyl), $C_2H_5$ (e.g. ethyl), $C_3H_7$ (e.g. propyl isomers such as propyl, isopropyl, etc.), $C_3H_6$ (e.g. cyclopropyl), $C_4H_9$ (e.g. butyl isomers) $C_4H_8$ (e.g. cyclobutyl isomers such as cyclobutyl, methylcyclopropyl, etc.), $C_5H_{11}$ (e.g. pentyl isomers), $C_5H_{10}$ (e.g. cyclopentyl isomers such as cyclopentyl, methylcyclobutyl, dimethylcyclopropyl, etc.) $C_6H_{13}$ (e.g. hexyl isomers), $C_6H_{12}$ (e.g. cyclohexyl isomers), $C_7H_{15}$ (e.g. heptyl isomers), $C_7H_{14}$ (e.g. cycloheptyl isomers), $C_8H_{17}$ (e.g. octyl isomers), $C_8H_{16}$ (e.g. cyclooctyl isomers), $C_9H_{19}$ (e.g. nonyl isomers), $C_9H_{18}$ (e.g. cyclononyl isomers), $C_{10}H_{21}$ (e.g. decyl isomers), $C_{10}H_{20}$ (e.g. cyclodecyl isomers), $C_{11}H_{23}$ (e.g. undecyl isomers), $C_{11}H_{22}$ (e.g. cycloundecyl isomers), $C_{12}H_{25}$ (e.g. dodecyl isomers), $C_{12}H_{24}$ (e.g. cyclododecyl isomers), $C_{13}H_{27}$ (e.g. tridecyl isomers), $C_{13}H_{26}$ (e.g. cyclotridecyl isomers), and the like.

An expression such as "$C_{1-12}$" (e.g. "$C_{1-12}$ hydrocarbyl") refers to the number of carbon atoms in a moiety, and similar expressions have similar meanings. Generally, an expression such as "$C_{1-12}$" refers only to the number of carbon atoms in a parent group, and does not characterize or limit the substituents in any way. For a hydrocarbyl moiety, the parent group includes all carbon atoms which are directly bonded to another carbon atom of the parent group (except for $C_1$ hydrocarbyl). For example, the carbon atoms which are counted are numbered in the moieties below:

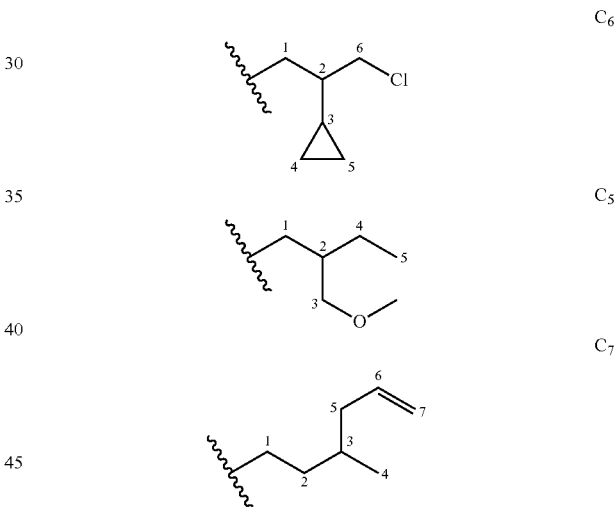

As used herein the term "bonding interaction" has the ordinary meaning understood by a person of ordinary skill in the art. In some embodiments, the term "bonding interaction" may include traditional covalent interactions or covalent bonds, or non-covalent interactions such as electron donor-acceptor interactions, dipole-dipole interactions, induced dipole-dipole interactions, hydrogen bonding, etc.

As used herein the term "acidic gas" has the ordinary meaning understood by a person of ordinary skill in the art. In some embodiments, the term "acidic gas" may include any gas which is acidic. In some embodiments, the acid gas may be more acidic than water, or may cause water to have a pH of less than about 7 when the gas is dissolved in water. In some embodiments, the acidic gas is an oxide of carbon such as carbon dioxide, carbon monoxide, and the like. In some embodiments, the acidic gas is an oxide of sulfur such as SO, $SO_2$, $SO_3$, and the like. In some embodiments, the acidic gas is an oxide of nitrogen such as $N_2O$, NO, $NO_2$, and the like.

As used herein, the phrase "a method of separating an acidic gas from a mixture of gases" should be construed to include any method which separates a composition comprising the acidic gas from the mixture of gases such that the purified gas comprises less of the acidic gas than it did prior to separation. In some embodiments, the method reduces the concentration or partial pressure of the acidic gas in the mixture of gases by at least about 20%, about 50%, about 90%, or about 99%.

As used herein the term "combustion product" has the ordinary meaning understood by a person of ordinary skill in the art. In some embodiments, the term "combustion product" may include any gases which are evolved as a product of a combustion reaction, such as a reaction of a carbon-based fuel including coal, a petroleum product, natural gas, etc. Examples of combustion products include oxides of elements such as carbon, sulfur, nitrogen, and the like.

Parameters such as the selectivity of absorption of an acidic gas, the ability to control absorption of an acidic gas, the reversibility of the absorption, and other related properties may be varied according to the application. Structural variations in ionic liquids may allow one or more of these parameters to be adjusted.

Some embodiments provide an ionic liquid comprising: optionally substituted pyrrolide, optionally substituted pyrazolide, optionally substituted indolide, optionally substituted phospholide, or optionally substituted imidazolide. In some embodiments, the ionic liquid comprises pyrrolide having 0, 1, or 2 substituents. In some embodiments, the ionic liquid comprises pyrazolide having 0 or 1 substituents. In some embodiments, the ionic liquid comprises indolide having 0, 1, 2, or 3 substituents.

In some embodiments, the anion is represented by Formula 1 or Formula 2, as depicted above.

With respect to Formula 1, X is N or P, A is N or $CR^3$, E is N or $CR^4$, G is N or $CR^5$, and J is N or $CR^6$. Thus, some embodiments relate to ionic liquids comprising an anion represented by Formula 3, Formula 4, Formula 5, or Formula 6.

Formula 3

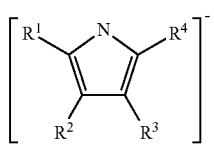

Formula 4

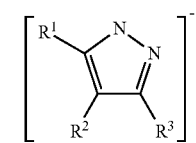

Formula 5

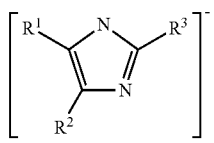

Formula 6

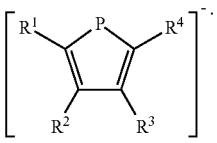

With respect to Formulas 1-6, although the formal charge of these structures may lie on an N or a P atom, it is believed that the actual distribution of the negative charge may include other atoms of the structure. Thus, the actual negative charge can be in any position or on any atom or combinations of atoms on the ion and still be within the scope of these formulas.

In some embodiments, an anion of a heteraromatic ring may form a covalent or non-covalent complex with carbon dioxide, such as an anion represented by Formula A, wherein ·· represents a covalent or non-covalent bonding interaction; and Het is optionally substituted heteroaryl. Some embodiments provide an ionic liquid comprising an anionic complex of optionally substituted pyrrolide and $CO_2$, optionally substituted pyrazolide and $CO_2$, optionally substituted indolide and $CO_2$, optionally substituted phospholide and $CO_2$, or optionally substituted imidazolide and $CO_2$.

In some embodiments, an anion of Formula 1, Formula 2, Formula 3, Formula 4, Formula 5, or Formula 6 may react with $CO_2$ to provide an anion represented by Formula 7, Formula 8, Formula 9, Formula 10, Formula 11, or Formula 12. Thus, some embodiments relate to ionic liquids comprising anions represented by any of Formulas 7-8, depicted above, and 9-12.

Formula 9

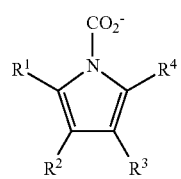

Formula 10

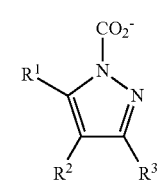

Formula 11

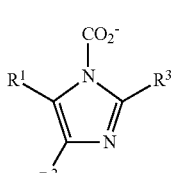

Formula 12

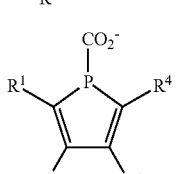

Reaction with other acidic gases, such as $SO_2$, would result in compounds similar to those in Formulas 7-12 where the $CO_2$ group is replaced by a group formed by the corresponding acid gas molecule.

With respect to Formulas 7-12, although the formal charge of these structures may lie on one or both of the oxygen atoms, it is believed that the actual distribution of the negative charge may include other atoms of the structure. Thus, the actual negative charge can be in any position or on any atom or combinations of atoms on the ion and still be within the scope of these formulas.

With respect to Formulas 1-12, $R^1$, $R^2$, $R^3$, $R^4$, $R^5$, $R^6$, $R^7$, $R^8$, $R^9$, and $R^{10}$ are independently halo, CN, CNO, NCO, $NO_2$, $R^{11}$, $OR^{11}$, $SR^{11}$, $NR^{12}R^{13}$, $-YC(O)ZR^{11}$, $SO_2R^{11}$, $SO_3R^{11}$, or $SO_2NR^{12}R^{13}$. Any of these groups on adjacent carbon atoms, e.g. $R^1$ and $R^2$, $R^2$ and $R^3$, $R^3$ and $R^4$, $R^5$ and $R^6$, $R^7$ and $R^8$, $R^8$ and $R^9$, $R^9$ and $R^{10}$, etc., may together form an aliphatic or an aromatic ring. For example, any of these pairs may, together with the parent ring atoms, form an additional optionally substituted phenyl ring, an optionally substituted cyclopentenyl ring, an optionally substituted hexenyl ring, an optionally substitute pyrrole ring, and the like. Thus, in some embodiments, the anion may comprise optionally substituted benzopyrrolide, optionally substituted benzopyrazolide, optionally substituted optionally substituted benzophospholide, or optionally substituted benzoimidazolide.

With respect to $R^1$, $R^2$, $R^3$, $R^4$, $R^5$, $R^6$, $R^7$, $R^8$, $R^9$, and $R^{10}$, Y is a single bond, optionally substituted $C_{1-6}$ hydrocarbyl, $-N(R^{12})-$, O, or S; Z is a single bond, $-N(R^{12})-$, O, or S; each $R^{11}$ is H or optionally substituted $C_{1-12}$ hydrocarbyl; and each $R^{12}$ and each $R^{13}$ is independently H or optionally substituted $C_{1-6}$ hydrocarbyl.

With respect to $-YC(O)ZR^{11}$, if Y is a single bond, the moiety may be represented by $-C(O)ZR^{11}$. In some embodiments, Y is optionally substituted $C_{1-6}$ hydrocarbyl, such as $C_{1-6}$ alkyl including $-(CH_2)_n-$ and $-C_nH_{2n}-$, wherein n is 1, 2, 3, 4, 5, or 6. Also with respect to $-YC(O)ZR^{11}$, if Z is a single bond, the moiety may be represented by $-YC(O)R^{11}$.

With respect to $R^1$, $R^2$, $R^3$, $R^4$, $R^5$, $R^6$, $R^7$, $R^8$, $R^9$, and $R^{10}$, $R^{11}$ may be H so that any of $R^{1-10}$ may independently be H, OH, SH, $-YC(O)ZH$, $SO_2H$, or $SO_3H$. In some embodiments, $R^{11}$ may be optionally substituted $C_{1-12}$ hydrocarbyl, such as $C_{1-12}$ alkyl, optionally substituted phenyl, optionally substituted naphthyl, or optionally substituted biphenyl. In some embodiments, each $R^{11}$ is independently H or $C_{1-3}$ alkyl.

With respect to $R^1$, $R^2$, $R^3$, $R^4$, $R^5$, $R^6$, $R^7$, $R^8$, $R^9$, and $R^{10}$, $R^{11}$, each $R^{12}$ and each $R^{13}$ may be independently H so that any of $R^{1-10}$ may independently be $NH_2$, $NHR^{12}$, or $SO_2NHR^{12}$. In some embodiments, $R^{12}$ and $R^{13}$ may independently be may be optionally substituted $C_{1-6}$ hydrocarbyl, such as $C_{1-6}$ alkyl or optionally substituted phenyl. In some embodiments, each $R^{12}$ and each $R^{13}$ is independently H or optionally substituted $C_{1-3}$ alkyl.

With respect to any of the combinations described above related to Formulas 1-12, in some embodiments, $R^1$, $R^2$, $R^3$, $R^4$, $R^5$, $R^6$, $R^7$, $R^8$, $R^9$, and $R^{10}$ are independently halo, CN, CNO, NCO, $NO_2$, $R^{11}$, $OR^{11}$, $SR^{11}$, $NR^{12}R^{13}$, $-C(O)R^{11}$, $-C(O)OR^{11}$, $-C(O)NR^{11}R^{12}$, $-OC(O)R^{11}$, $-OC(O)OR^{11}$, $-OC(O)NR^{11}R^{12}$, $-N(R^{12})C(O)R^{11}$, $-N(R^{12})C(O)OR^{11}$, $-N(R^{12})C(O)SR^{11}$, $-N(R^{12})C(O)NR^{11}R^{12}$, $-SO_2R^{11}$, $-SO_3R^{11}$, or $-SO_2NR^{11}R^{12}$. In some embodiments, $R^1$ is F, $CF_3$, $CHF_2$, $CH_2F$, CN, $CO_2CH_3$, acetyl, or trichloroacetyl. In some embodiments, $R^2$ is F, $CF_3$, $CHF_2$, $CH_2F$, CN, $CO_2CH_3$, acetyl, or trichloroacetyl.

In some embodiments, the ionic liquid comprises at least one anion selected from: 2-fluoropyrrolide, 2-trifluoromethylpyrrolide, 1-fluoromethylpyrrolide, 2-cyanopyrrolide, 1-difluoromethylpyrrolide, 1-fluoropyrrolide, 1-trifluoromethylpyrazolide, 1-cyanopyrrolide, 1-methylesterpyrrolide, 1-trifluoromethylpyrrolide, 1-acetylpyrrolide, and 1-trichloroacetylpyrrolide.

These anions may be in ionic liquids which may be used for removing or separating an acidic gas from a mixture of gases. In some embodiments, the ionic liquid may be mixed with one or more addition diluents, wherein the ionic liquid acts as the active ingredient for removing or separating the acidic gas from a mixture of gases. In many of these uses, it may be desirable to first remove the acidic gas from the mixture of gases, and then remove the acidic gas from the ionic liquid so that the acidic gas may be collected or used and/or so that the ionic liquid may be reused. Thus, in many embodiments, the particular use may require the strength of the binding interaction between the ionic liquid and the acidic gases to be tuned to optimize the conditions under which the acidic gas is taken up and released by the ionic liquid.

While not limiting any embodiment, it is believed that the binding strength between $CO_2$ (or other acidic gas) and the ionic liquid may be tuned by varying the substituents on the ionic liquid. Generally, it is believed that an electron-withdrawing substituent on an anion of a heteroaryl ring can reduce strength of the binding interaction between the ionic liquid and $CO_2$. This may allow easier recovery of $CO_2$ after it has been absorbed by the ionic liquid. Thus, in some embodiments, the anion of a heteroaryl ring may have at least one electron-withdrawing substituent. Examples of electron withdrawing substituents may include, but are not limited to, F, $CF_3$, $CHF_2$, $CH_2F$, CN, $CO_2CH_3$ or other carboxyalkyl esters, acetyl or other acyl groups, trichloroacetyl, etc. Conversely, it is also believed than an electron-donating substituent on an anion of a heteroaryl ring can increase the strength of the binding interaction on an anion of a heteroaryl ring. This may provide easier absorption of $CO_2$ (or other acidic gas) by the ionic liquid. It is also believed that a substituent on the carbon immediately adjacent to a heteroatom of the anion of a heteroaryl ring has a greater effect on the binding strength than a substituent on a carbon which is more remote. For example, with respect to Formula 3, an electron withdrawing $R^1$ will reduce the strength of the binding to $CO_2$ more than an electron withdrawing $R^2$. Thus, the binding strength may be tuned by varying the number, position, and nature of the substituents on the anion using these principles.

In some embodiments, the cations present in the ionic liquid may be selected to tune properties of the ionic liquid such as decomposition temperature, density, viscosity, melting point, heat capacity, and the like. Furthermore, in some embodiments, the cation may also be selected to be chemically active towards carbon dioxide. The cation present in the ionic liquid can be a single species or a plurality of different species. Both of these embodiments are intended to be embraced, unless otherwise specified, by the use of the singular expression "cation." The cations of the ionic liquid include organic and inorganic cations. Examples of cations include quaternary nitrogen-containing cations, phosphonium cations, and sulfonium cations. Suitable cations include those disclosed in U.S. Pat. No. 7,053,232 and US Publication No. 2005/0131118, the disclosures of which are hereby incorporated by reference in their entireties.

Examples of quaternary nitrogen-containing cations include, but are not limited to, cyclic, aliphatic, and aromatic quaternary nitrogen-containing cations such as n-alkyl pyridinium, a dialkyl pyrrolidinium, a dialkyl imidazolium, or an alkylammonium of the formula $R'_{4-X}NH_X$ wherein X is 0-3 and each R' is independently an alkyl group having 1 to 18 carbon atoms. In some embodiments, unsymmetrical cations may provide lower melting temperatures. Examples of phosphonium cations include, but are not limited to, cyclic, aliphatic, and aromatic phosphonium cations. For example, the phosphonium cations include those of the formula $R''_{4-X}PH_X$ wherein X is 0-3, and each R'' is an alkyl or aryl group such as an alkyl group having 1 to 18 carbon atoms or a phenyl group. Examples of sulfonium cations include, but are not limited to cyclic, aliphatic, and aromatic sulfonium cations. For example, the sulfonium cations include those of the formula $R'''_{3-X}SH_X$ wherein X is 0-2 and each R''' is an alkyl or aryl group such as an alkyl group having 1 to 18 carbon atoms or a phenyl group. Additional more specific examples may include, but are not limited to, ammonium, imidazolium, phosphonium, 1-butyl-3-methylimidazolium, 1-decyl-3-methylimidazolium, 1-dodecyl-3-methylimidazolium, 1-ethyl-3-butyl imidazolium, 1-hexyl-3-methylimidazolium, 1-hexylpyridinium, 1-methy-3-butyl imidazolium, 1-methy-3-decyl imidazolium, 1-methy-3-dodecyl imidazolium, 1-methy-3-ethyl imidazolium, 1-methy-3-hexadecyl imidazolium, 1-methy-3-hexyl imidazolium, 1-methy-3-octadecyl imidazolium, 1-methy-3-octyl imidazolium, 1-methy-3-propyl imidazolium, 1-octyl-3-methylimidazolium, 1-octylpyridinium, benzyl pyridinium, N-butyl pyridinium, ethyl pyridinium, and ethylene pyridinium. Other examples of suitable cations are known in the art. For example, US2006/0197053, US2008/0028777, and US2007/0144186, all of which are incorporated by reference in their entireties, describe a number of suitable cations, and any of these cations may be used with an anion described herein.

The ionic liquids described herein may be used in a number of methods related to gas separation, purification, or other uses related to the uptake of an acidic gas by an ionic liquid.

Ionic liquids have relatively low vapor pressures. Thus, under some conditions, they are not volatilized to a significant extent into a purified gas stream. Their low vapor pressure minimizes loss of absorbing material during use and provides a simple mechanism for regeneration, such as by heating, distillation, evacuation, and/or by extraction with a supercritical fluid.

For example, one embodiment provides a method of separating an acidic gas from a mixture of gases, comprising: providing sufficient contact between the mixture of gases and an ionic liquid described herein to allow at least a portion of the acidic gas to be absorbed by the ionic liquid to provide a purified gas; and collecting or diverting for use the purified gas and/or the acidic gas. In some embodiments, the mixture of gas comprises a combustion product or a combustion exhaust, such as a combustion product of a fossil fuel or other carbon-based fuel such as oil, gasoline, petroleum products, natural gas, other hydrocarbons, coal, methanol, ethanol, other alcohols, and the like. In some embodiments, the acidic gas is an oxide of carbon, an oxide of sulfur, or an oxide of nitrogen. In some embodiments, the acidic gas may be CO, $CO_2$, SO, $SO_2$, $SO_3$, $N_2O$, NO, $NO_2$, etc.

When sufficient contact is provided between the mixture of gases and the ionic liquid, the acidic gas is absorbed by the ionic liquid to provide a purified gas. Absorption of the acidic gas by the ionic liquid includes absorption without reaction, or it may include absorbing the acidic gas in a manner that causes the acidic gas to decompose, or react with the ionic liquid or another solute in the ionic liquid. For example, absorption may provide anions such as those depicted in Formulas 7-12. In some embodiments, the ionic liquids described herein may have the advantage that the viscosity of the liquid remains relatively low as $CO_2$ is absorbed by the ionic liquid. In some embodiments, an ionic liquid may have a viscosity less than about 10,000 cP, about 5,000 cP, or about 1,000 cP at a temperature of about 20° C. and under a $CO_2$ pressure of about 1 bar. In some embodiments, an ionic liquid may have a viscosity less than about 1,000 cP, about 500 cP, or about 200 cP at a temperature of about 50° C. and under a $CO_2$ pressure of about 1 bar. In some embodiments, exposure of the ionic liquid to a $CO_2$ pressure of about 1 bar may increase the viscosity by less than about 10 times, about 5 times, or about 2 times as compared to the viscosity of the ionic liquid before exposure to the $CO_2$.

The temperature, pressure, and time of absorption may vary. In some embodiments, the temperature may be about 0° C., about 10° C., about 20° C., or about 50° C., up to about 100° C., about 150° C., about 200° C., or about 300° C., including from about 0° C. to about 300° C., from about 0° C. to about 100° C., and other ranges including and bordered by the preceding values. In some embodiments, the pressure may be in the range of about $10^{-4}$ bar to about 10 bar, $10^{-4}$ bar to about 1.0 bar, or about $10^{-4}$ bar to about 0.1 bar and also includes pressures between such values and ranges including and bordered by the preceding values. In some embodiments, the contacting of gas and ionic liquid material may be carried out for about 0.1 s to 100 hr, 1 s hr to 10 hr, or 10 s hr to about 1 hr, about 1 min to about 10 hr, or about 1 min to about 5 hr and also includes times between such values and ranges including and bordered by the preceding values.

In some embodiments, the acidic gas, such as $CO_2$, may be removed from the ionic liquid by heating the ionic liquid and/or applying reduced pressure to the liquid. For example, that amount of acidic gas that some ionic liquids can absorb may substantially decrease as temperature is increased. Thus, increasing the temperature of an ionic liquid with absorbed acidic gas may cause a substantial amount of the acidic gas to be released from the ionic liquid. In some embodiments, the ionic liquid may be heated to a temperature of at least about 40° C., about 50° C., or about 100° C., up to about 150° C., about 200° C., or about 300° C.

Similarly, the amount of acidic gas that some ionic liquids can absorb may substantially decrease as pressure is reduced. Thus, reducing the pressure of an ionic liquid with absorbed acidic gas may cause a substantial amount of the acidic gas to be released from the ionic liquid. In some embodiments, the pressure may be in the range of about $10^{-4}$ bar to about 10 bar, $10^{-4}$ bar to about 1.0 bar, or about $10^{-4}$ bar to about 0.1 bar.

In some embodiments, the heating and/or applying reduced pressure may be carried out for about 0.1 s to 100 hr, 1 s to 10 hr, or 10 s to about 1 hr, about 1 min to about 10 hr, or about 1 min to about 5 hr. Thus, the ionic liquid may be reused.

In some embodiments, once the acidic gas is absorbed, the acidic gas and/or the purified gas mixture may be collected or diverted for use. The acidic gas may be collected for storage or use by applying reduced pressure and/or heat to the ionic liquid, as described above. In some embodiments, $CO_2$ may be collected and stored, such as in carbon capture and sequestration. In some embodiments, an acidic gas may be absorbed and the purified gas mixture may be diverted for a use. For example, the mixture of gases may be natural gas containing impurities such as water and carbon dioxide and sulfur-containing compounds. After the carbon dioxide, water and sulfur compounds are absorbed by the ionic liquid, the purified natural gas may be diverted for various industrial uses. In another example, in the first step of producing purified nitrogen from air, impurities such as water and carbon dioxide may be removed using a method or an ionic liquid described herein. Subsequent separation of the oxygen and nitrogen may be performed by cryogenic distillation.

Figure 2:
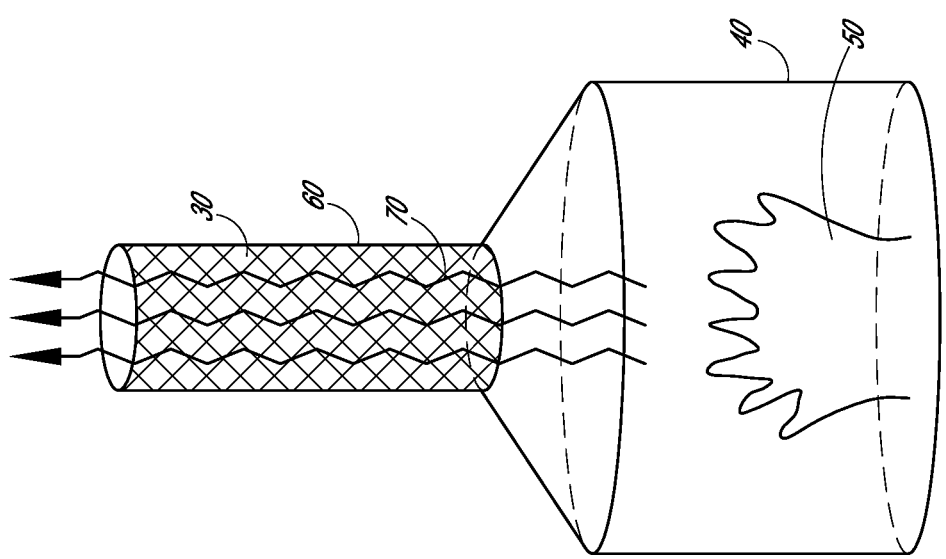
FIG. 2 is an example of an embodiment of a combustion device described herein.

FIG. 1 is a schematic diagram of an embodiment of a gas separation device. A flow component 10 is provided which is configured to provide a flow of a mixture of gases 15. The flow component 10 may be any component which is capable of providing a flow of gas or a mixture of gases such as a pump, a pressurized container, a combustion vessel, etc. The flow component is in fluid communication with a separation component 20, and the separation component is configured to allow a flow of a mixture of gases to pass through the separation component 20 from the flow component 10. In some embodiments, the flow of the mixture of gases may pass directly from the flow component 10 through the separation component 20. However, in other embodiments, the flow may pass through other components of the device after exiting the flow component 10 and before passing through the separation component 20. An ionic liquid 30 is coupled to the separation component 20, and the device is configured to provide sufficient contact between the mixture of gases and the ionic liquid to remove at least a portion of the acidic gas from the mixture of gases. FIG. 2 is a schematic diagram of an embodiment of a combustion device. The combustion device comprises a combustion vessel 40 configured to contain a combustion reaction 50. An exhaust component 60, is in fluid communication with the combustion vessel 40, and is configured to allow exhaust 70 from the combustion vessel 40 to escape from the combustion vessel 40. The exhaust 70 may be a mixture of gases comprising an acidic gas. An ionic liquid 30 is coupled to the exhaust component 60, and the device is configured to provide sufficient contact between the exhaust 70 and the ionic liquid 30 to remove at least a portion of the acidic gas from the exhaust.

Figure 3:
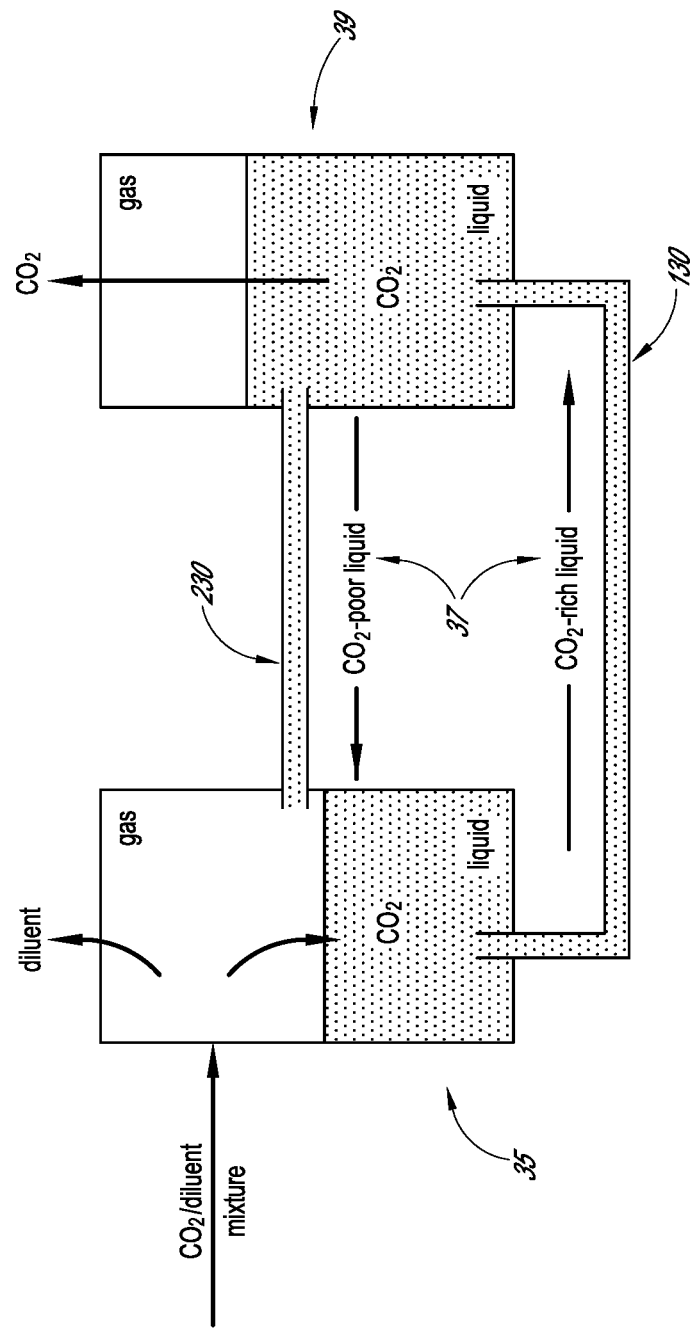
FIG. 3 is an example of an embodiment of a circulation system described herein.

In some embodiments, the devices depicted by FIG. 1 and FIG. 2 may further comprise a circulation system, as depicted in FIG. 3. The absorption unit 35, such as the separation component 20 of FIG. 1 or the exhaust component 70 of FIG. 2, may be coupled to a circulation system 37 which circulates $CO_2$-rich ionic liquid 130 to a desorption unit 39, such as a high temperature stripper, which removes the acidic gas from the ionic liquid by a method described above. $CO_2$-poor ionic liquid 230 is then circulated from the desorption unit 39 to the absorption unit 35.

There are many ways that the ionic liquid 30 may be coupled to the separation component 20 or the exhaust component 70 so that the device is configured to provide sufficient contact is provided between the mixture of gases and the ionic liquid to effect the desired separation. For example, the ionic liquid may coat at least part of an interior surface of the separation component 20 or the exhaust component 70. In some embodiments, a flow of the ionic liquid on the interior surface may be provided. In some embodiments, a particulate solid substrate coated with the ionic liquid may be coupled to the separation component or the exhaust component to increase the surface area of the ionic liquid in contact with the mixture of gases. The ionic liquid may be part of the separation component 20 or the exhaust component 30, or may be a separate feature which is attached or otherwise coupled to, and/or in fluid communication with, the separation component 20 or the exhaust component 30. In some embodiments, the process may be selected or the device may be configured to promote intimate mixing of the liquid ionic compound with the source gas. In embodiments, sufficient contact may be provided by allowing the contact to occur for a time sufficient to allow significant removal of acidic gas. Thus, in some embodiments, systems maximizing surface area contact may be used. For example, in some embodiments, sufficient contact may be provided by permeation through a supported liquid membrane, or by use of conventional liquid absorbers, such as counter-current liquid absorbers and the like.

Supported liquid membranes comprise a solvent such as an ionic liquid contained within the pores of a solid microporous support, such as a ceramic, metal, or polymeric support. In some embodiments, supported liquid membranes fabricated from supports such as ceramics, metals, and certain heat stable polymers may be used in higher than ambient temperature operations. In some embodiments, such higher temperature operations may effect a more rapid separation, requiring less contact time. In addition, these higher temperature operations may also be a consequence of the process configuration, such as configurations requiring purification of high temperature exhaust gases or other gases exiting high temperature operations. Supported liquid membranes suitable for purifying high temperature gases may obviate the need to pre-cool such gases before contact with the supported liquid membrane. Microporous supports suitable for use in the present methods and their methods of preparation are well known in the art (see, for example, U.S. Pat. Nos. 3,426,754; 3,801,404; 3,839,516; 3,843,761; 3,843,762; 3,920,785; 4,055,696; 4,255,376; 4,257,997; 4,359,510; 4,405,688 and 4,438,185, the disclosures of which are hereby incorporated by reference).

In some embodiments, the ionic liquid may be used in a conventional gas/liquid absorption unit-based system comprising a fixed bed. Such systems can be operated in batch mode or continuous flow mode. In a typical batch mode configuration, the ionic liquid may be introduced into a vessel followed by introduction of the mixture of gases. After a prescribed residence time, the resulting gas is removed, leaving behind the acidic gas dissolved in the ionic liquid. The acidic gas can be collected by heating and/or reduced pressure treatment. To increase contact between the ionic liquid and the mixture of gases, the ionic liquid can be coated on a solid support, such as glass beads, and the like, to increase the surface area of the ionic liquid capable of contacting the mixture of gases.

In some embodiments, the ionic liquid may be contacted with the mixture of gases in a flow apparatus. The above batch processes may be adapted for flow where the flow rate through the vessel correlates to the residence time of contact and may be suitably chosen to afford an effluent stream with the desired purification tolerance. When the ionic liquid has sufficiently absorbed the acidic gas the acidic gas can be collected by heating and/or vacuum as described.

In some embodiments, to promote intimate mixing, gas/liquid absorption units also may be operated in a dual flow mode. In some embodiments, the dual flow can be co-current or counter-current. In these embodiments, the mixture of gases and the ionic liquid may flow through a purification unit contemporaneously. In either the co-current or the counter-current aspects, the acidic gas may be removed from the contacted ionic liquid prior to reintroduction to the purification unit.

Some embodiments provide a method of cooling an enclosed volume comprising compressing and expanding a gas, such as one comprising carbon dioxide, in the presence of an ionic liquid described herein. In some embodiments, the gas may be the refrigerant, and an ionic liquid described herein may be an absorbent, as described with respect to the methods and devices of US2007/0144186 and US2006/0197053, which are expressly incorporated by reference herein in their entireties. Furthermore, any device described in those documents may be adapted for use herein.

Synthetic Methods

While many methods may be used to prepare the ionic liquids described herein, one convenient method is to obtain the neutral form of the anion, e.g. a heteroaromatic compound such as a substituted pyrrole, an optionally substituted pyrazole, an optionally substituted indole, an optionally substituted phosphole, an optionally substituted imidazole, etc., and to deprotonate the neutral form with a hydroxide salt of a phosphonium ion. Many neutral heteroaromatic compounds may be obtained from commercial sources (e.g., Pyrrole-2-carbonitrile (96%), 2-acetylpyrrole (98%), methyl 2-pyrrolecarboxylate (97%), 3-(trifluoromethyl)pyrazole (99%)) can be purchased from Sigma-Aldrich) or prepared using methods known in the art, such as by nucleophilic or electrophilic aromatic substitution methods. The phosphonium hydroxides may be prepared by a number of methods, known in the art, such as by anion exchange of a phosphonium halide. Many phosphonium halides may be obtained from commercial sources (e.g., CYPHOS IL 102, [$P_{66614}$][Br]) from Cytec Industries, Inc).

Example 1

Synthesis of Trihexyl(Tetradecyl)Phosphonium Cyanopyrrolide, [$P_{66614}$][2-CNpyr]:

The synthesis of [$P_{66614}$][2-CNpyr] is typical of a method that may be used to prepare many of the ionic liquids described herein. The phosphonium salt, [$P_{66614}$][Br], is diluted with methanol (2M) and then transformed to [$P_{66614}$][OH] by adding 2:1 molar equivalents of an anion exchange resin (e.g., DOWEX SBR LC NG (OH) ion exchange resin from Dow Chemical Company) in three batches, allowing 12 hrs in between. The resin is pretreated with 1:1 volume equivalent of methanol by rinsing 3 times at room temperature since the resin is unstable at temperatures above 60° C. During the ion exchange step, the mixture is stirred gently without a stir bar (which could deform the resin beads). After filtration to remove the resin, the [$P_{66614}$][OH] solution is mixed with a 1:1 molar equivalent of pyrrole-2-carbonitrile and stirred for 12 hrs. This produces the [$P_{66614}$][2-CNpyr] and water. Excess methanol is removed by rotary evaporator at 50° C. and the [$P_{66614}$][2-CNpyr] solution is further dried under vacuum for 72 hrs at 50° C. Similar procedures are followed with other heterocyclic anion precursors to make other ionic liquids described herein.

Example 2

Density functional theory (B3LYP/6-311G++(d,p)) was used as an indicator of the reaction energy between carbon dioxide and the anion of the ionic liquid for different substituents. In these calculations, the structures and energies of the unreacted anion, reacted anion, and $CO_2$ were combined to estimate the overall reaction energy ($\Delta E$).

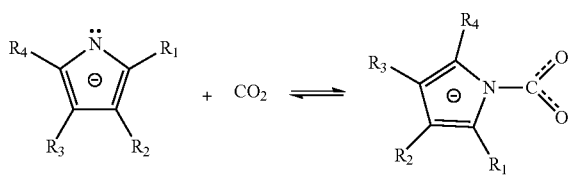

$\Delta E = E_{product} - E_{CO2} - E_{reactant}$

Table 1 shows representative results for an unsubstituted pyrrolide anion (e.g. the anion of pyrrole) and various monosubstituted pyrrolide anions. The calculated reaction energy for the parent pyrrolide is $-99$ kJ mol$^{-1}$. While not limiting any embodiment, it is believed that electronegative substituents withdraw charge from the pyrrolide, decrease the anion —$CO_2$ bond energy, and increase the reaction energy. For instance, placing fluorine in the $R_2$ position (2-fluoropyrrolide) or $R_1$ (1-fluoropyrrolide) positions increases the reaction energy to $-89$ and $-46$ kJ mol$^{-1}$, respectively. As can be seen from the Table, other substituents (CN, $CH_xF_{3-x}$, . . . ) have similar effects. It is believed that similar trends will be seen with anions or other heteraryl rings, such as the imidazolides or pyrazolides.

TABLE 1

| Reactant name | Reactant Structure | B3LYP ΔH (kJ/mol) | Calorimetric ΔH (kJ/mol) |
|---|---|---|---|
| Pyrrolide |  | −99 |  |
| 2-fluoro-pyrrolide |  | −89 |  |
| 2-trifluoro-methylpyrrolide |  | −67 |  |
| 1-fluoromethyl-pyrrolide |  | −67 |  |
| 2-cyano-pyrrolide |  | −59 |  |
| 1-difluoro-methyl-pyrrolide |  | −58 |  |
| 1-fluoro-pyrrolide |  | −46 |  |
| 1-trifluoro-methyl-pyrazolide |  | −44 | −45 |
| 1-cyano-pyrrolide |  | −35 | −48 |

TABLE 1-continued

| Reactant name | Reactant Structure | B3LYP ΔH (kJ/mol) | Calorimetric ΔH (kJ/mol) |
|---|---|---|---|
| 1-methylester-pyrrolide | | −33 | −10 |
| 1-trifluoro-methylpyrrolide | | −32 | |
| 1-acetyl-pyrrolide | | −28 | |
| 1-trichloro-acetylpyrrolide | | 1 | |

Figure 4:
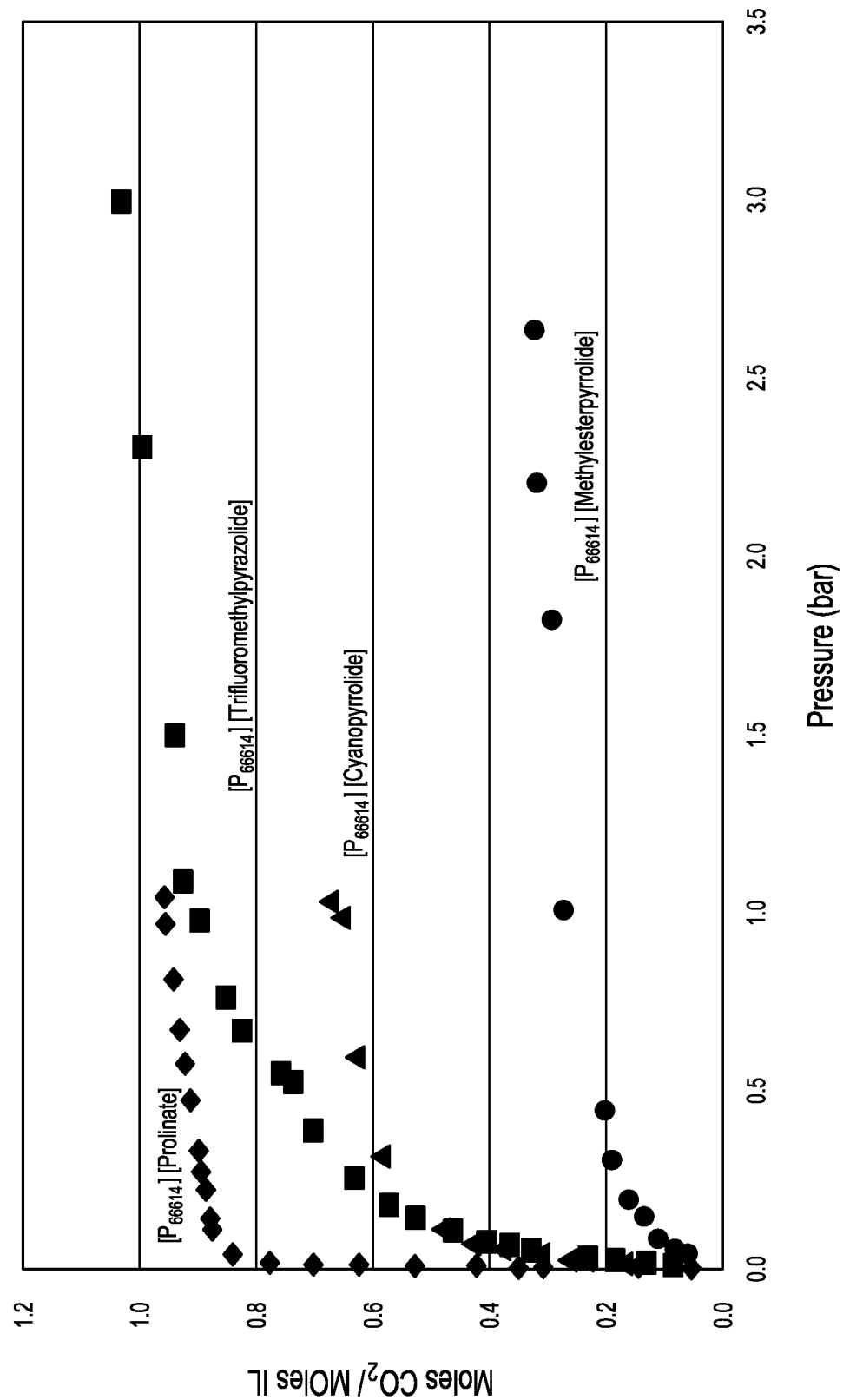
FIG. 4 is a plot of moles $CO_2$ absorbed/moles of ionic liquid against $CO_2$ pressure in bars for some embodiments of the ionic liquids described herein.

It was believed that a lower, i.e. more negative, calculated ΔE may correspond to stronger binding or more absorption of carbon dioxide. Thus, it is believed that the calculated ΔE may provide a good model for tuning $CO_2$ absorption based upon the substituents used on the anionic ring. To test this model, absorption isotherms (moles of $CO_2$/moles ionic liquid plotted against $CO_2$ pressure) were measured for three different substituted pyrrolides. FIG. 4 provides a plot of these isotherms. The plots show that the weakest binding, seen as a smaller slope of moles $CO_2$/moles ionic liquid versus $CO_2$ pressure, was observed for methylesterpyrrolide, which had the highest calculated ΔE (−33 kJ/mole). It was also seen that cyanopyrrolide, which had an intermediate calculated ΔE (−35 kJ/mole), had intermediate binding. Finally, trifluoromethylpyrazolide, which had the lowest calculated ΔF (−44 kJ/mole), had the strongest binding. Also shown on the graph is $[P_{66614}]$[Prolinate], an amino acid based ionic liquid control. It has a much lower calculated ΔE (−71 kJ/mol from calculations and −77 kJ/mol from calorimetry), consistent with the steep slope.

FIG. 4 also shows that the isotherms maximize near 1:1 mole ratio, which may be evidence that the anion reacts with $CO_2$ to obtain a $CO_2$ substituted ion as depicted in Formulas 7-12.

Calorimetric studies of $CO_2$ absorption enthalpies were also performed for the same three compounds, and results are shown in Table 1. Again, the results qualitatively agree with the experimental results depicted in FIG. 3, especially when uncertainties in both the computed numbers and the experiments are considered.

Similar studies may also be done using acidic gases other than $CO_2$.

Example 3

Figure 5:
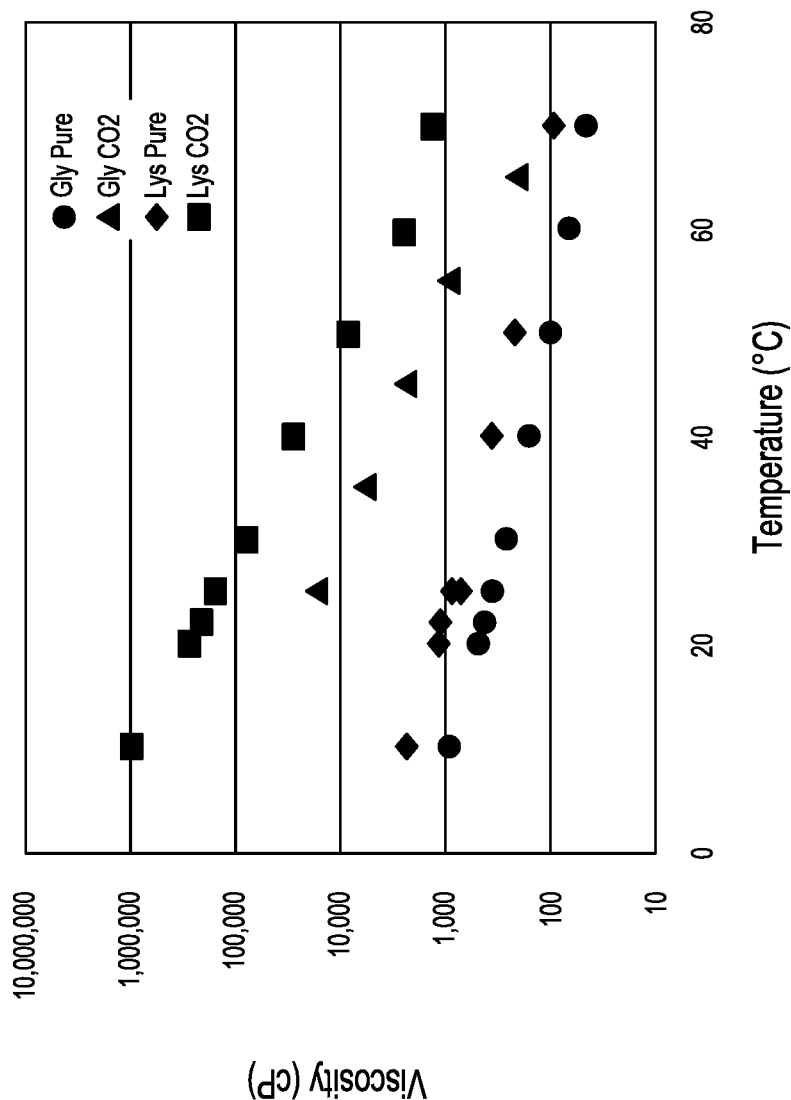
FIG. 5 is a plot of viscosity (cP) against temperature (° C.) for two control ionic liquids comprising amino acid anions.

The viscosity of control ionic liquids comprising glycinate or lysinate under 0 bar and 1 bar pressure of $CO_2$ is plotted against temperature in FIG. 5. Like most amino acid based ionic liquids (e.g. those published previously in the literature), these ionic liquids exhibit a large increase in viscosity when the $CO_2$ pressure is increased from 0 bar to 1 bar. While not limiting any embodiment, these large viscosity increases may make use of these ionic liquids to separate of $CO_2$ from other gases or absorb $CO_2$ more difficult in industrial processes.

Example 4

Figure 6:
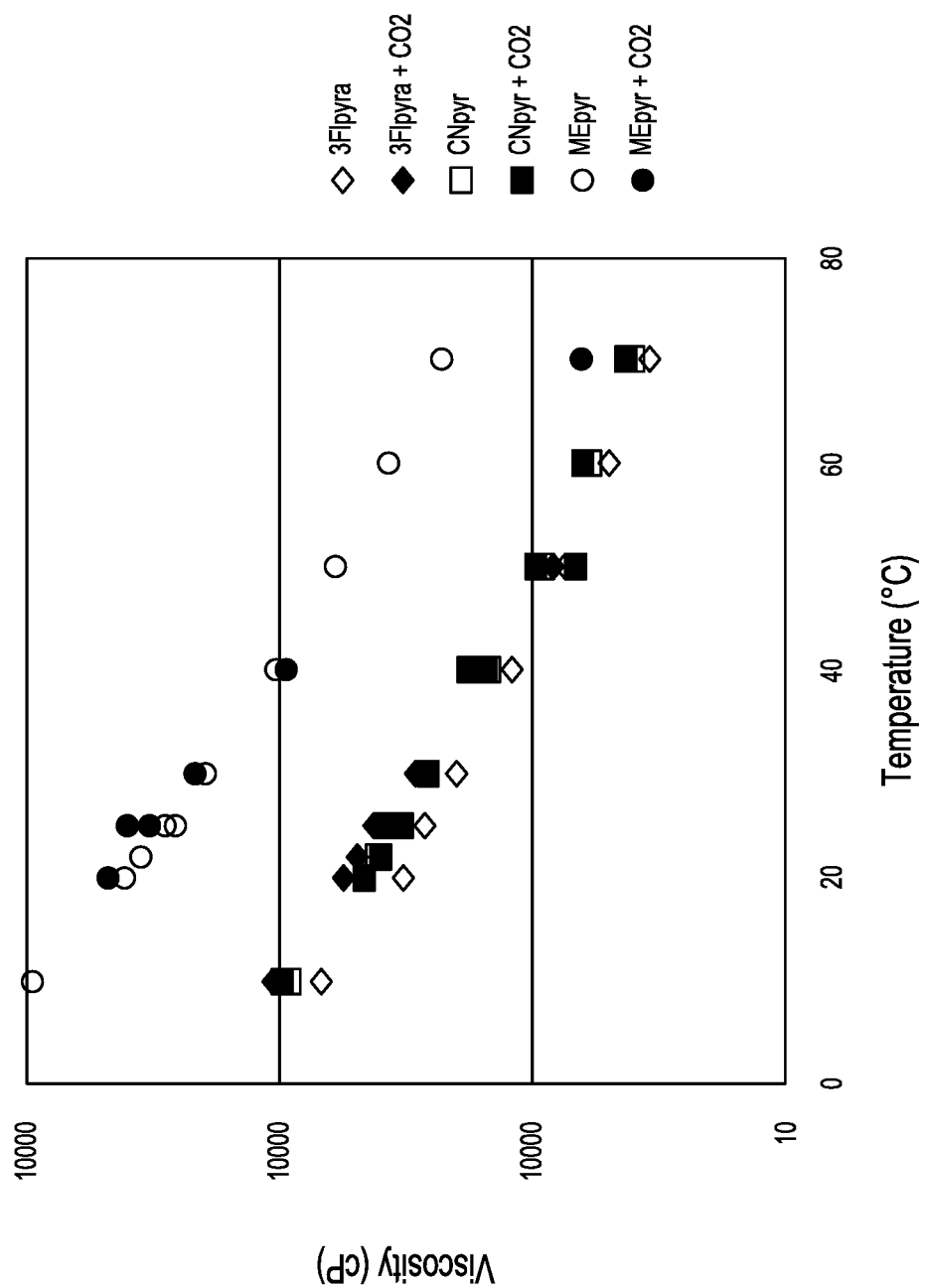
FIG. 6 is a plot of viscosity (cP) against temperature (° C.) for some embodiments of the ionic liquids described herein.

The viscosity of $[P_{66614}]$[methylesterpyrrolide], $[P_{66614}]$[cyanopyrrolide], and $[P_{66614}]$[trifluoromethylpyrazolide] with 0 bar pressure of $CO_2$ and with 1 bar pressure of $CO_2$ is plotted in FIG. 6. The viscosity increases for these compounds is much smaller than those observed for the control ionic liquids.

Example 5

Figure 7:
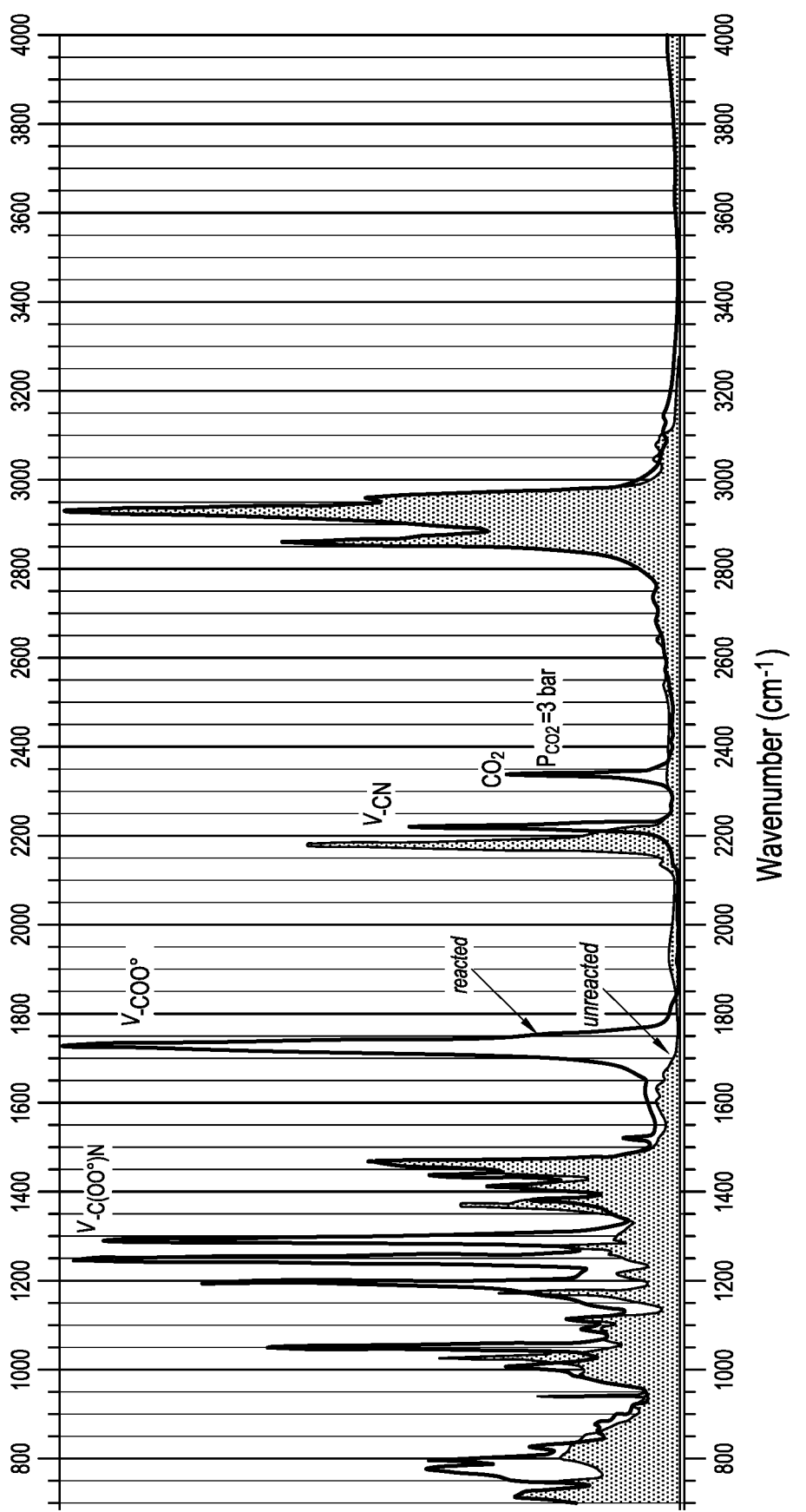
FIG. 7 is a plot of the infrared (IR) spectrum of an embodiment of ionic liquid described herein before and after reaction with carbon dioxide.

Trihexyl(tetradecyl)phosphonium 2-cyanopyrrolide ($[P_{66614}]$[2-CNpyr]), a stable ionic liquid, was synthesized as described in Example 1 above. The $[P_{66614}]$[2-CNpyr] was reacted with $CO_2$ at a pressure of about 1 bar. FIG. 7 is a plot of the infrared (IR) spectrum of the ionic liquid before and after reaction. The unreacted ionic liquid has a feature at about 2183 $cm^{-1}$, which may be characteristic of a CN group. After reaction, the CN band shifts to about 2220 $cm^{-1}$, and prominent peaks appear at about 1728 $cm^{-1}$ and about 1200 $cm^{-1}$ to about 1300 $cm^{-1}$ which may indicate —$NCOO^-$ stretches. At about 3 bar pressure, a band due to physically dissolved $CO_2$ appeared between about 2470 $cm^{-1}$ and 2300 $cm^{-1}$. Application of a vacuum caused the IR spectrum to be restored to that observed before reaction.

Figure 8:
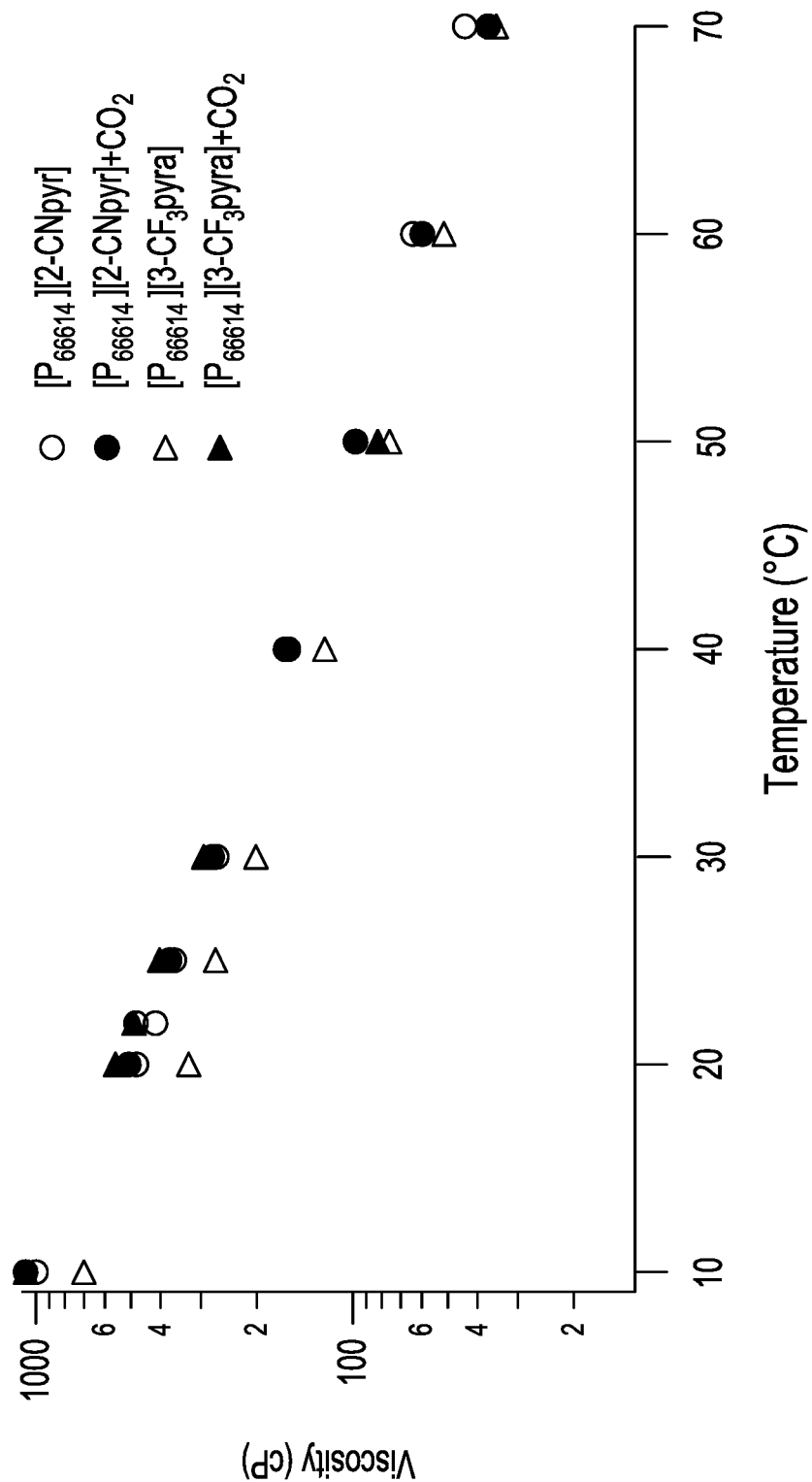
FIG. 8 is a plot of viscosity (cP) against temperature (° C.) for some embodiments of the ionic liquids described herein before exposure to carbon dioxide and under 1 bar of carbon dioxide.
Figure 9:
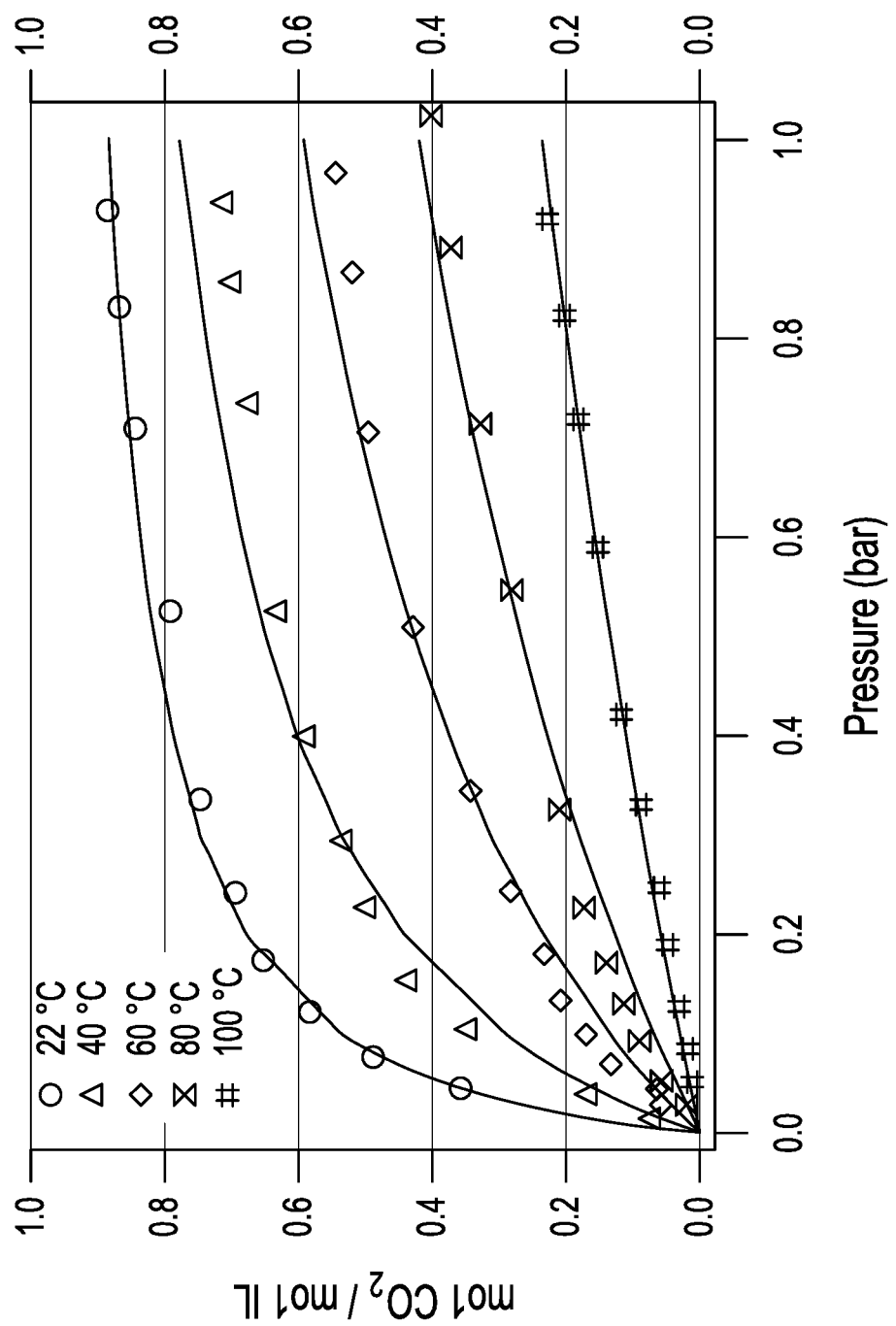
FIG. 9 is a plot of moles of carbon dioxide absorbed against carbon dioxide pressure by an embodiment of ionic liquid disclosed herein at several different temperatures.

FIG. 8 shows that the viscosity of $[P_{66614}]$[2-CNpyr] under 1 bar $CO_2$ is about the same as unreacted $[P_{66614}]$[2-CNpyr] for at least the temperature range of about 10° C. to about 70° C. FIG. 9 shows the isotherms of $[P_{66614}]$[2-CNpyr] at various temperatures. The steep initial slopes may reflect chemical reaction between $CO_2$ and the $[P_{66614}]$[2-CNpyr]. The gradual slopes at higher pressure may reflect the contribution of weaker physical absorption. The uptake approaches 1 mole $CO_2$ per mole $[P_{66614}]$[2-CNpyr] at the highest pressures and lowest temperatures shown, consistent with a 1:1 stoichiometry. At higher temperatures, the uptake goes above 1 mole $CO_2$ per mole $[P_{66614}]$[2-CNpyr], which is believed to be due to increased $CO_2$ physical solubility with increasing pressure.

Figure 10:
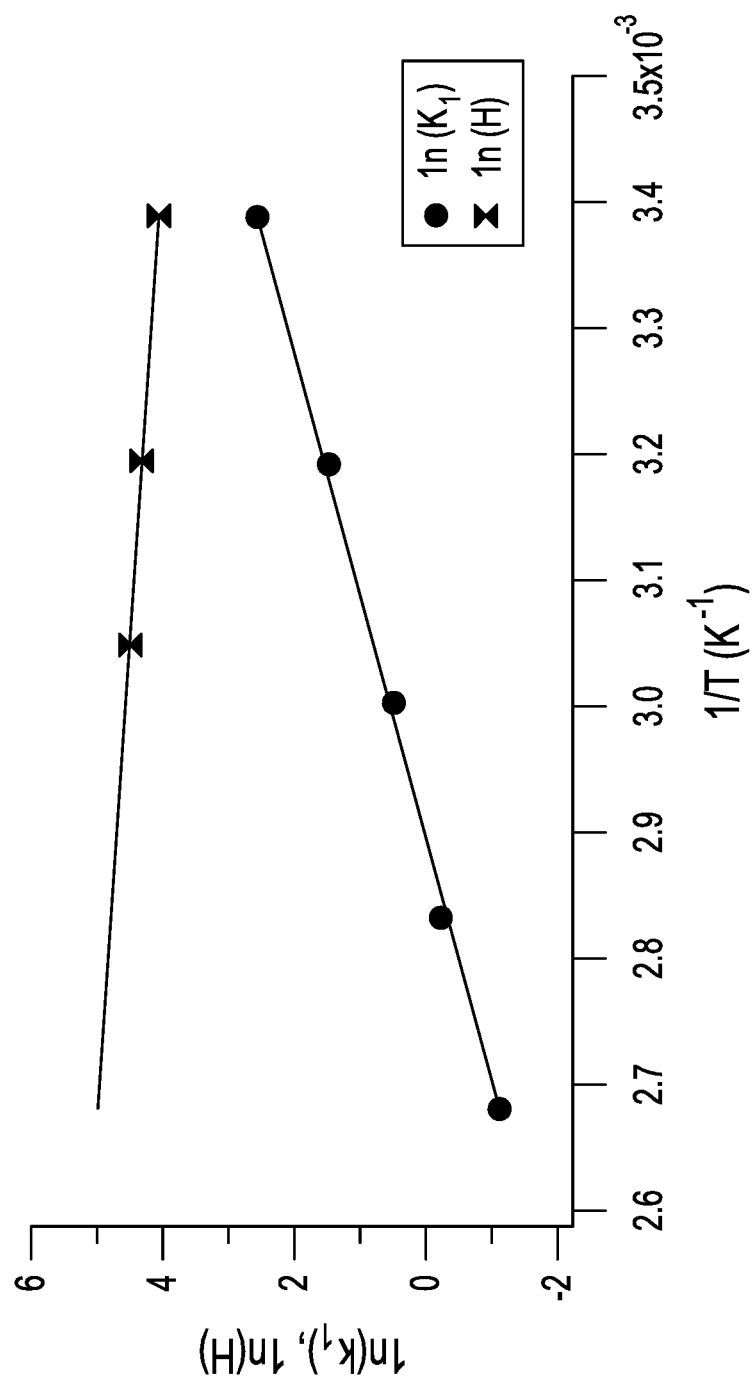
FIG. 10 is a plot of ln(k1) or ln(H) against 1/T (K−1) for an embodiment of ionic liquid disclosed herein.

The data of FIGS. 7-9 were used to obtain the Henry's law constant (H) and reaction equilibrium constant ($k_1$) for the reaction at various temperatures. These are plotted in FIG. 10. Based upon this information, the chemical reaction enthalpy this reaction is believed to be about 43 kJ $mol^{-1}$ and the entropy is believed to be about 130 J $mol^{-1}$ $K^{-1}$. Differential scanning calorimetry gave a reaction enthalpy of about −53 kJ $mol^{-1}$, which agrees with the data obtained from the isotherms.

Example 6

Figure 11:
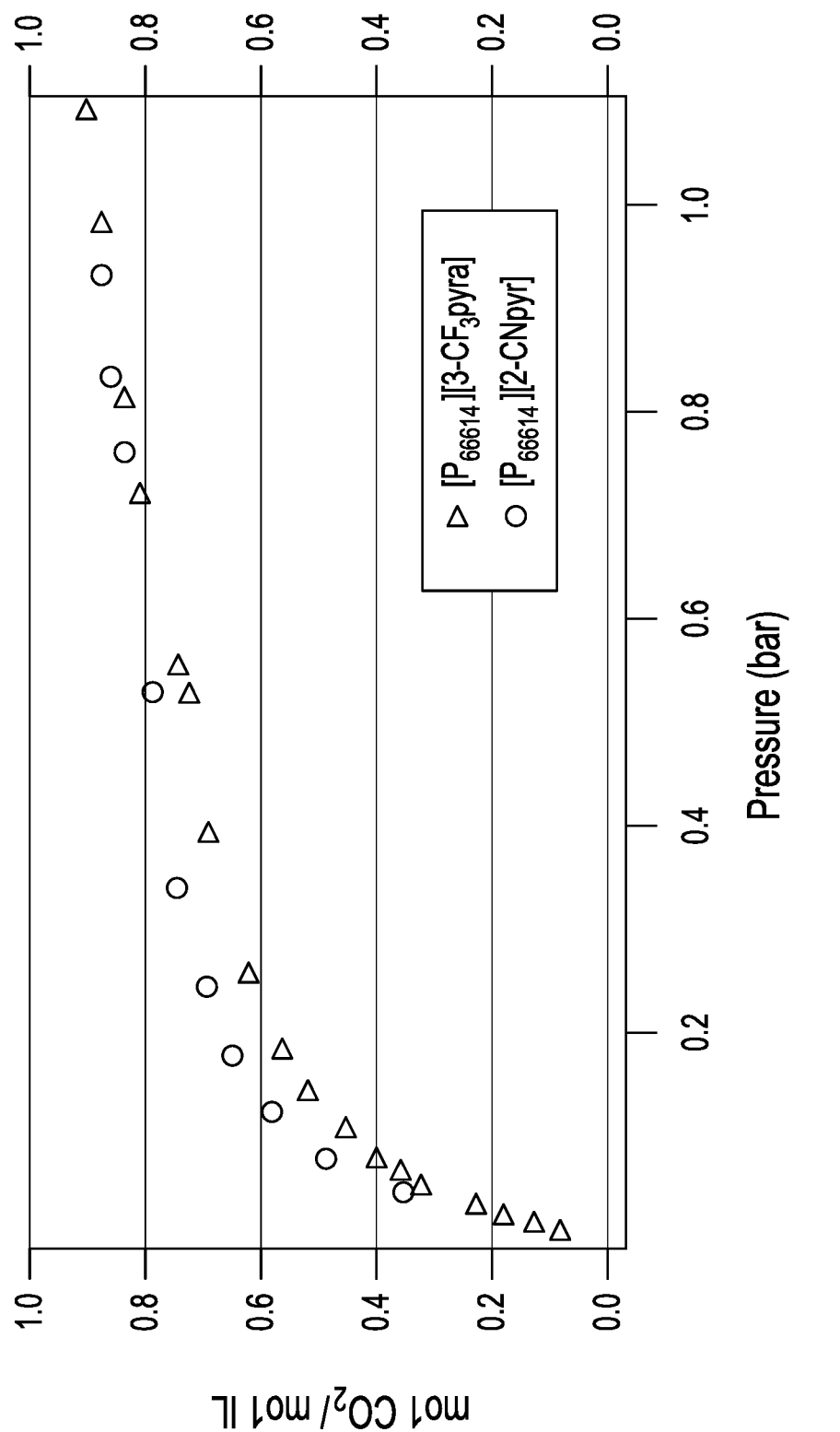
FIG. 11 is a plot of moles of carbon dioxide absorbed against carbon dioxide pressure by some embodiment of ionic liquid disclosed herein.

Trihexyl(tetradecyl)phosphonium 3-(trifluoromethyl)pyrazolide $[P_{66614}]$[2-$CF_3$-pyra] was prepared using a procedure described in Example 1. The viscosity data for this ionic liquid is also included in FIG. 8. FIG. 11 compares the isotherms of $[P_{66614}]$[2-CNpyr] and $[P_{66614}]$[2-$CF_3$-pyra] at 22° C. The reaction enthalpy of $CO_2$ with [2-$CF_3$-pyra] was determined to be about −46 kJ $mol^{-1}$ by calorimetry.

It is believed that similar viscosity properties will be observed for other ionic liquids described herein. This may make the ionic liquids described herein much more attractive for commercial applications.

While the above detail description has shown, described, and pointed out novel features of the invention as applied to various embodiments, it will be understood that various omissions, substitutions, and changes in the form and details of the systems, methods, processes, or compositions illustrated may be made by those skilled in the art without departing from the spirit of the invention. As will be recognized, the present invention may be embodied within a form that does not provide all of the features and benefits set forth herein, as some features may be used or practiced separated from others.

What is claimed is:

1. An ionic liquid comprising an anion represented by a formula:

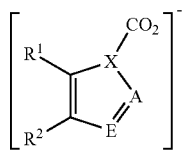

wherein X is N;
A is N or $CR^3$;
E is N or $CR^4$;
$R^1$, $R^2$, $R^3$, and $R^4$ are each independently H, halo, CN, CNO, NCO, $NO_2$, $R^{11}$, $OR^{11}$, $SR^{11}$, $NR^{12}R^{13}$, —YC(O)$ZR^{11}$, $SO_2R^{11}$, $SO_3R^{11}$, or $SO_2NR^{12}R^{13}$;
Y is a single bond, optionally substituted $C_{1-6}$ hydrocarbyl, —N($R^{12}$)—, O, or S;
Z is a single bond, —N($R^{12}$)—, O, or S;
each $R^{11}$ is H or optionally substituted $C_{1-12}$ hydrocarbyl; and
each $R^{12}$ and each $R^{13}$ is independently H or optionally substituted $C_{1-6}$ hydrocarbyl.

2. The ionic liquid of claim 1, wherein $R^1$ and $R^4$ are H and $R^2$ is $NO_2$.

3. A method of removing carbon dioxide from a mixture of gases, comprising:
providing a mixture of gases comprising carbon dioxide; and
allowing sufficient contact between the mixture of gases and a first ionic liquid comprising an anion according to the formula

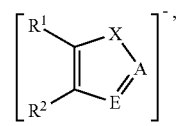

wherein:
X is N;
A is N or $CR^3$;
E is N or $CR^4$; and
$R^1$, $R^2$, $R^3$, and $R^4$ are each independently H, halo, CN, CNO, NCO, $NO_2$, $R^{11}$, $OR^{11}$, $SR^{11}$, $NR^{12}R^{13}$, —YC(O)$ZR^{11}$, $SO_2R^{11}$, $SO_3R^{11}$, or $SO_2NR^{12}R^{13}$;
Y is a single bond, optionally substituted $C_{1-6}$ hydrocarbyl, —N($R^{12}$)—, O, or S;
Z is a single bond, —N($R^{12}$)—, O, or S;
each $R^{11}$ is H or optionally substituted $C_{1-12}$ hydrocarbyl; and
each $R^{12}$ and each $R^{13}$ is independently H or optionally substituted $C_{1-6}$ hydrocarbyl;

such that the carbon dioxide reacts with the first ionic liquid to form a second ionic liquid according to claim 1, thereby reducing the amount of carbon dioxide in the mixture of gases.

4. The method of claim 3, wherein the mixture of gases is an exhaust from combustion of a carbon-based fuel, wherein the carbon-based fuel is coal, a petroleum product, or natural gas.

5. The method of claim 3, wherein the mixture of gases further comprises an oxide of sulfur or nitrogen.

6. The method of claim 3, further comprising recovering the carbon dioxide from the second ionic liquid by applying at least one of heat or reduced pressure to the second ionic liquid.

7. A gas separation system comprising:
a flow component configured to provide a flow of a gas mixture, wherein the gas mixture comprises carbon dioxide; and
a separation component, in fluid communication with the flow component, configured to allow the flow of the gas mixture to pass through the separation component from the flow component, wherein a quantity of a first ionic liquid is contained within or coupled to the separation component, wherein the first ionic liquid comprises a first anion according to the formula

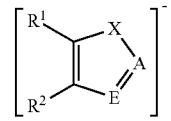

wherein:
X is N;
A is N or $CR^3$;
E is N or $CR^4$;
$R^1$, $R^2$, $R^3$, and $R^4$ are each independently H, halo, CN, CNO, NCO, $NO_2$, $R^{11}$, $OR^{11}$, $SR^{11}$, $NR^{12}R^{13}$, —YC(O)$ZR^{11}$, $SO_2R^{11}$, $SO_3R^{11}$, or $SO_2NR^{12}R^{13}$;
Y is a single bond, optionally substituted $C_{1-6}$ hydrocarbyl, —N($R^{12}$)—, O, or S;
Z is a single bond, —N($R^{12}$)—, O, or S;
each $R^{11}$ is H or optionally substituted $C_{1-12}$ hydrocarbyl; and
each $R^{12}$ and each $R^{13}$ is independently H or optionally substituted $C_{1-6}$ hydrocarbyl;
and
wherein the system is configured to provide sufficient contact between the gas mixture and the first ionic liquid to remove at least a portion of the carbon dioxide from the gas mixture and thereby form a second ionic liquid comprising a second anion represented by a formula

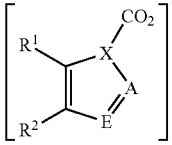

wherein X is N;
A is N or $CR^3$;

E is N or $CR^4$;

$R^1$, $R^2$, $R^3$, and $R^4$ are each independently H, halo, CN, CNO, NCO, $NO_2$, $R^{11}$, $OR^{11}$, $SR^{11}$, $NR^{12}R^{13}$, —YC(O)$ZR^{11}$, $SO_2R^{11}$, $SO_3R^{11}$, or $SO_2NR^{12}R^{13}$;

Y is a single bond, optionally substituted $C_{1-6}$ hydrocarbyl, —N($R^{12}$)—, O, or S;

Z is a single bond, —N($R^{12}$)—, O, or S;

each $R^{11}$ is H or optionally substituted $C_{1-12}$ hydrocarbyl; and each $R^{12}$ and each $R^{13}$ is independently H or optionally substituted $C_{1-6}$ hydrocarbyl; and wherein the system contains the second ionic liquid.

8. The gas separation system of claim 7, further comprising a regeneration component wherein the second ionic liquid is subjected to heat and/or reduced pressure to liberate carbon dioxide.

9. A combustion device comprising:

a combustion vessel configured to contain a combustion reaction;

an exhaust component, in fluid communication with the combustion vessel, which is configured to allow exhaust from the combustion reaction to escape from the combustion vessel, wherein the exhaust comprises carbon dioxide; and the gas separation system of claim 7, coupled to the exhaust component;

wherein the device is configured to provide sufficient contact between the exhaust and the separation system to remove at least a portion of the carbon dioxide from the exhaust.

* * * * *